(12) United States Patent
Ganz et al.

(10) Patent No.: US 8,163,238 B2
(45) Date of Patent: Apr. 24, 2012

(54) AUTOMATED MICRO-WELL PLATE HANDLING DEVICE

(75) Inventors: Brian L. Ganz, Carlsbad, CA (US); Nicholas P. Pratte, San Marcos, CA (US); Anthony L. Moore, Encinitas, CA (US); Chinapong Songchan, La Mesa, CA (US)

(73) Assignee: Let's Go Robotics, Inc., Carlsbad, CA (US)

( * ) Notice: Subject to any disclaimer, the term of this patent is extended or adjusted under 35 U.S.C. 154(b) by 1581 days.

(21) Appl. No.: 11/224,488

(22) Filed: Sep. 12, 2005

(65) Prior Publication Data

US 2007/0059205 A1 Mar. 15, 2007

(51) Int. Cl.
*G01N 33/00* (2006.01)
*G01N 33/48* (2006.01)

(52) U.S. Cl. ......... 422/63; 422/98; 422/400; 435/286.2; 435/287.3; 435/303.1; 141/1; 141/129; 141/130

(58) Field of Classification Search .................. 422/102, 422/63, 99, 400; 435/286.2, 287.3, 303.1; 141/1, 129, 130
See application file for complete search history.

(56) References Cited

U.S. PATENT DOCUMENTS

| 4,507,044 A | 3/1985 | Hutchins |
| RE32,414 E | 5/1987 | Hutchins |
| 5,096,564 A * | 3/1992 | Jowitt et al. .................. 204/625 |
| 6,637,473 B2 * | 10/2003 | Ganz et al. .................... 141/130 |
| 2006/0177922 A1 * | 8/2006 | Shamah et al. ............ 435/286.2 |

* cited by examiner

*Primary Examiner* — Krishnan S Menon
*Assistant Examiner* — Rebecca M Fritchman
(74) *Attorney, Agent, or Firm* — John R. Ross; John R. Ross, III

(57) ABSTRACT

An automated micro-well plate handling device for removing a micro-well plate from within a vertically stacked plurality of micro-well plates and transferring the removable micro-well plate to a receiving area. A vertical storage device for storing the vertically stacked plurality of micro-well plates creates a vertical clearance space between the vertically stacked micro-well plates. A shovel slides into the vertical clearance space underneath the micro-well plate that is being removed. The shovel then removes the micro-well plate from the vertical storage device and places the micro-well plate at a transfer station. A gripper then grabs the micro-well plate from the transfer station and transfers the micro-well plate to a receiving area. In a preferred embodiment, the automated micro-well plate handling device is controlled via a computer network.

17 Claims, 34 Drawing Sheets

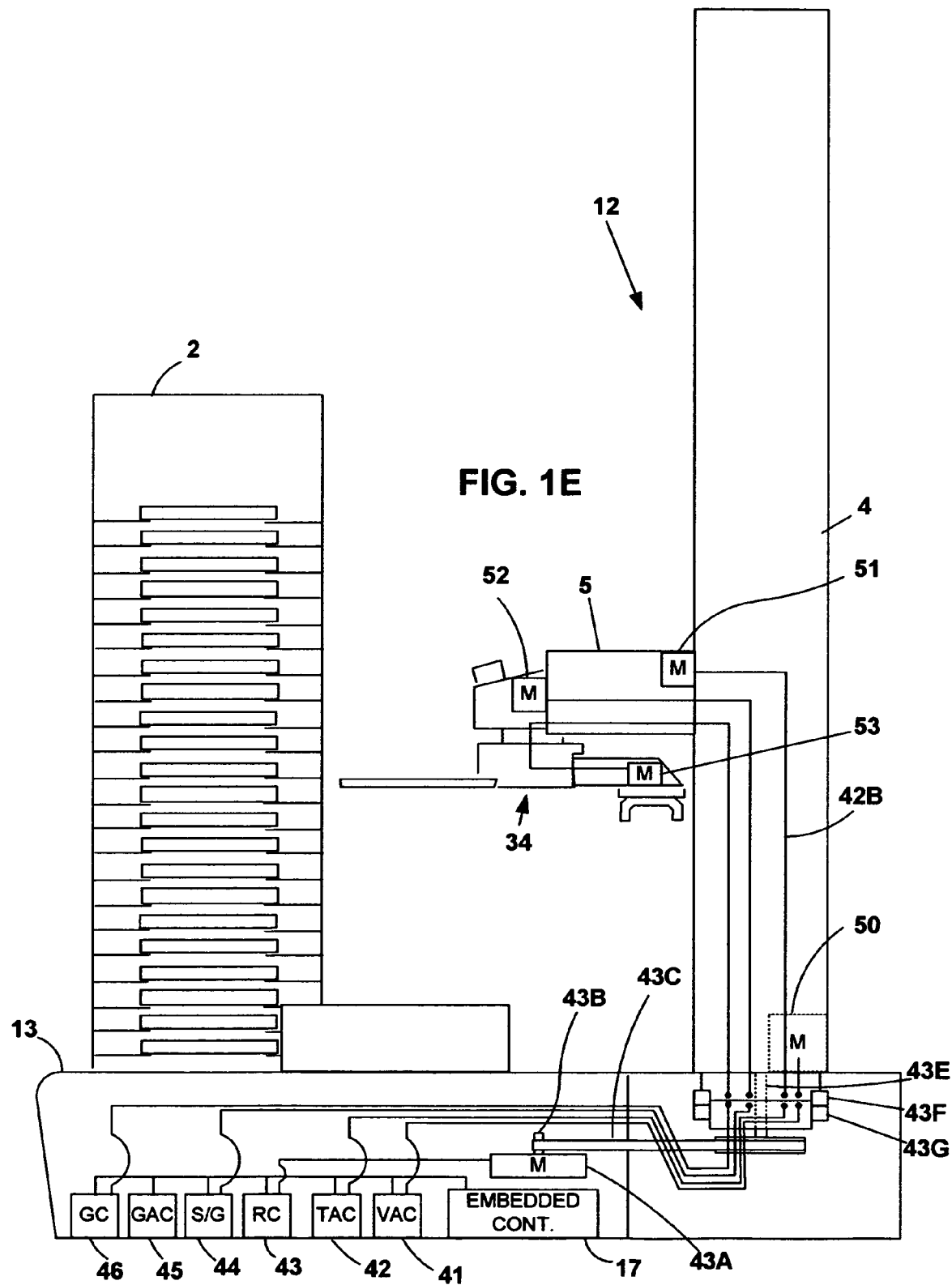

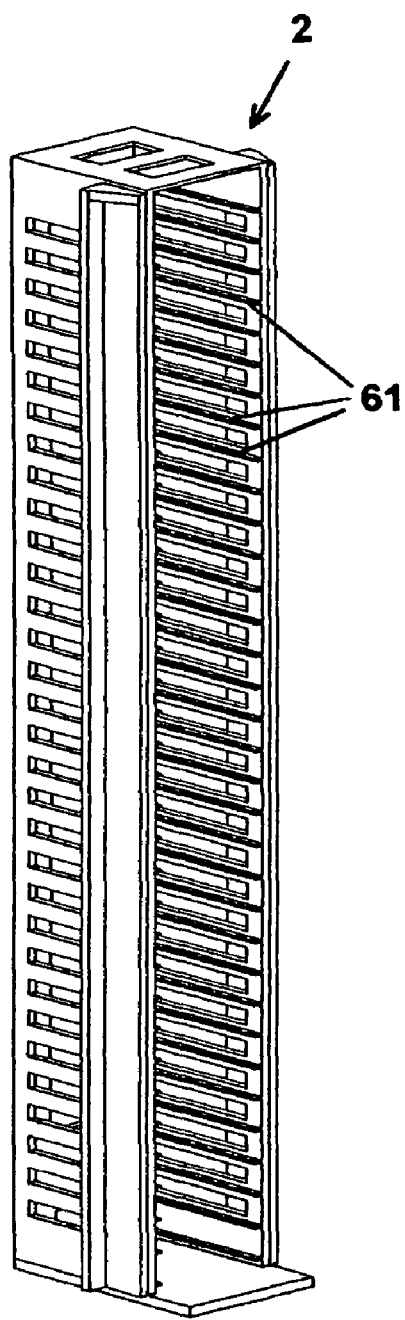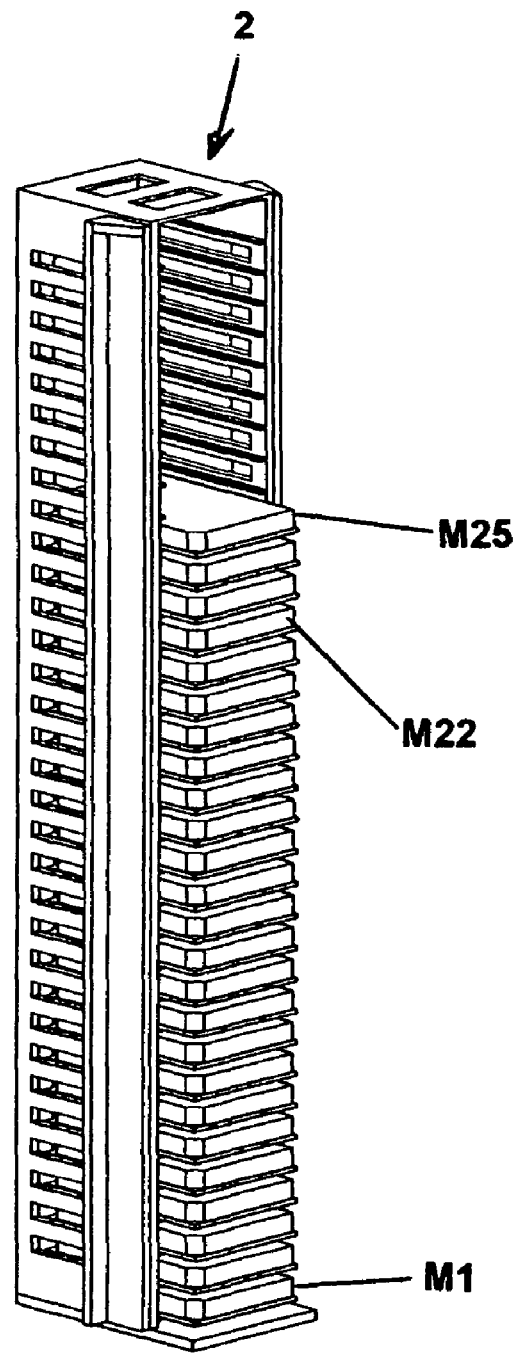
FIG. 1F  FIG. 1G

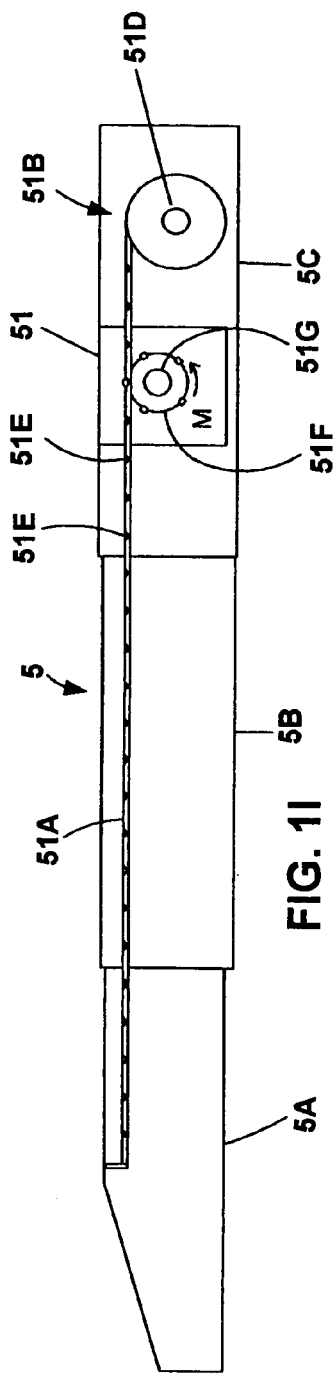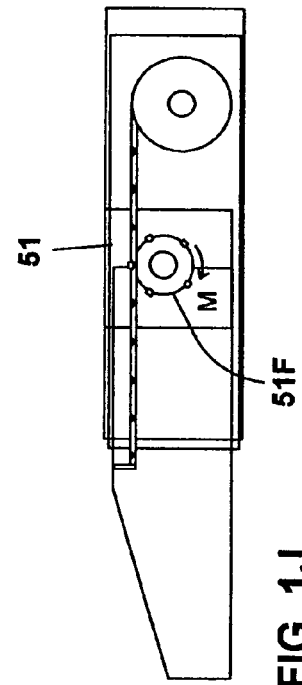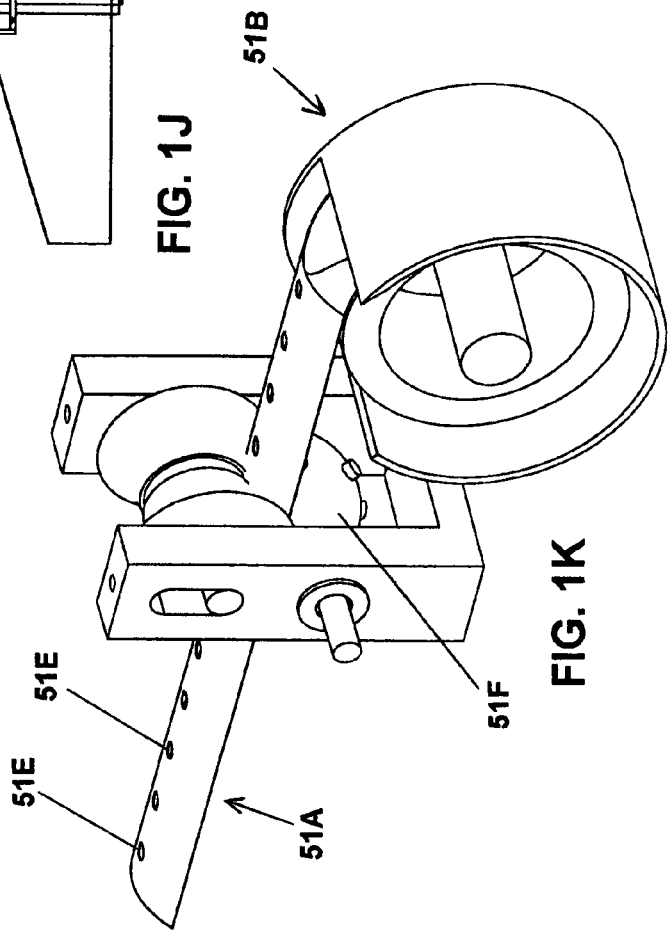

AUTOMATED MICRO-WELL PLATE HANDLING DEVICE

The present invention relates to micro-well plate handling devices, and in particular to automated micro-well plate handling devices.

BACKGROUND OF THE INVENTION

The prior art includes automated devices that are capable of handling micro-well plates. However, these devices are cumbersome for some handling requirements. For example, prior art micro-well plate handling devices require that in order to remove an individual micro-well plate from within a vertical stack of micro-well plates that all the micro-well plates above the micro-well plate are first removed and then set aside. This can be a very time consuming and tedious process.

Computer Network

A computer network is a data communications system that interconnects computer systems at various different sites. There are many types of computer networks. Some of these are described below:

The Internet

The Internet, or simply the Net, is the publicly available worldwide system of interconnected computer networks that transmit data by packet switching using a standardized Internet Protocol (IP) and many other protocols. It is made up of thousands of smaller commercial, academic, and government networks. It carries various information and services, such as electronic mail, online chat and the interlinked web pages and other documents of the World Wide Web.

An Intranet

An Intranet is a private network that is contained within an enterprise. It may consist of many interlinked local area networks (LAN) and also use leased lines in the Wide Area Network (WAN). Typically, an Intranet includes connections through one or more gateway computers to the outside Internet. The main purpose of an Intranet is to share company information and computing resources among employees. An Intranet can also be used to facilitate working in groups and for teleconferences.

An Ethernet

An Ethernet is the most widely-installed local area network (LAN) technology. An Ethernet LAN typically uses coaxial cable or special grades of twisted pair wires. The most commonly installed Ethernet systems are called 10BASE-T and provide transmission speeds up to 10 Mbps. Devices are connected to the cable and compete for access using a Carrier Sense Multiple Access with Collision Detection (CSMA/CD) protocol.

Slip Ring

Slip rings are known. A slip ring is an electrically conductive ring which is used around a shaft to conduct current from a rotating part to a non-rotating part as with generators or electric motors.

What is needed is a better automated micro-well plate handling device.

SUMMARY OF THE INVENTION

The present invention provides an automated micro-well plate handling device for removing a micro-well plate from within a vertically stacked plurality of micro-well plates and transferring the removable micro-well plate to a receiving area. A vertical storage device for storing the vertically stacked plurality of micro-well plates creates a vertical clearance space between the vertically stacked micro-well plates. A shovel slides into the vertical clearance space underneath the micro-well plate that is being removed. The shovel then removes the micro-well plate from the vertical storage device and places the micro-well plate at a transfer station. A gripper then grabs the micro-well plate from the transfer station and transfers the micro-well plate to a receiving area. In a preferred embodiment, the automated micro-well plate handling device is controlled via a computer network.

BRIEF DESCRIPTION OF THE DRAWINGS

FIGS. 1A-1E, and 1H-1N show a first preferred embodiment of the present invention.
FIGS. 1F and 1G show a micro-well plate storage unit.

DETAILED DESCRIPTION OF THE PREFERRED EMBODIMENTS

Figure 1A:
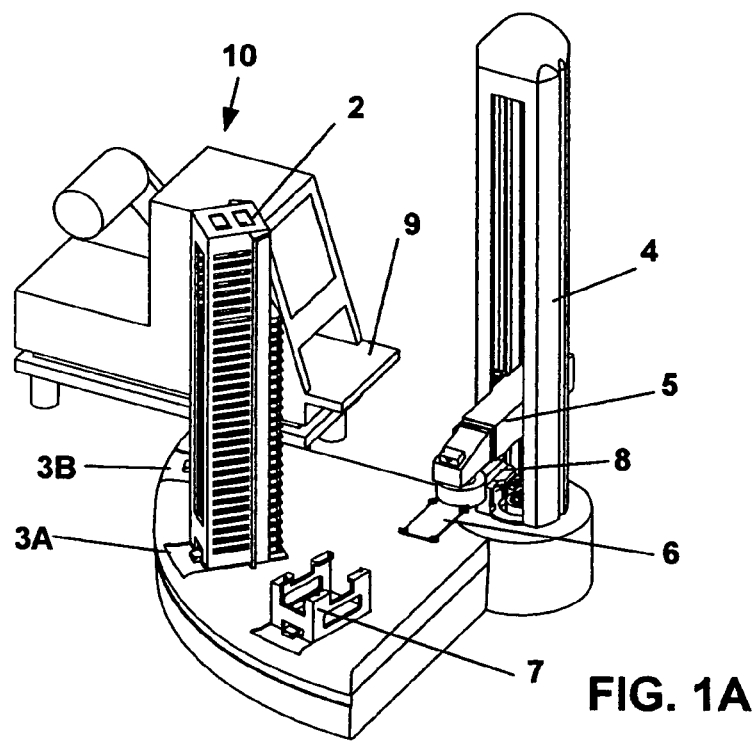

FIG. 1A shows a perspective view of a preferred embodiment of the present invention. In the preferred embodiment shown in FIG. 1A, micro-well plate handling robot 12 removes a micro-well plate from the middle of micro-well plate storage unit 2 and places it on platform 9 of receiving machine 10. Telescopic gripper arm 5 extends into micro-well plate storage unit 2 and shovel 6 (FIG. 1B) removes a micro-well plate from micro-well plate storage unit 2. Shovel 6 then lays the removed micro-well plate at transfer station 7 (FIG. 1A). Gripper 8 (FIG. 1C) then rotates so that it is above the micro-well plate at transfer station 7. Gripper 8 then grabs the micro-well plate, lifts it, and places the micro-well plate on platform 9 of receiving machine 10.

Preferred Connectivity

Figure 1B:
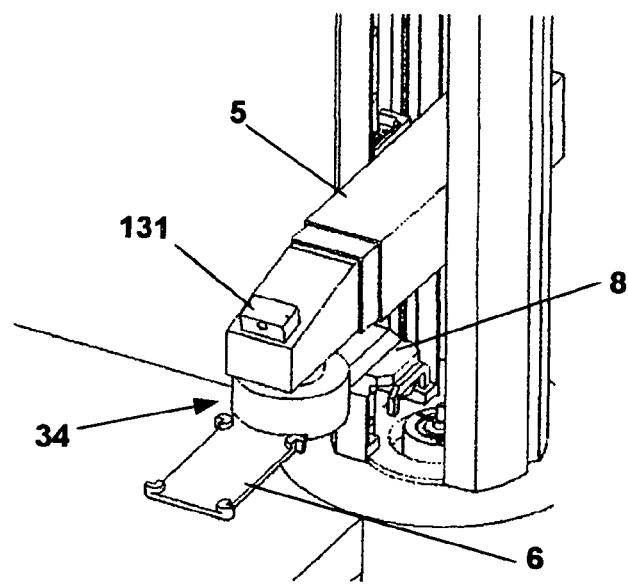
Figure 1C:
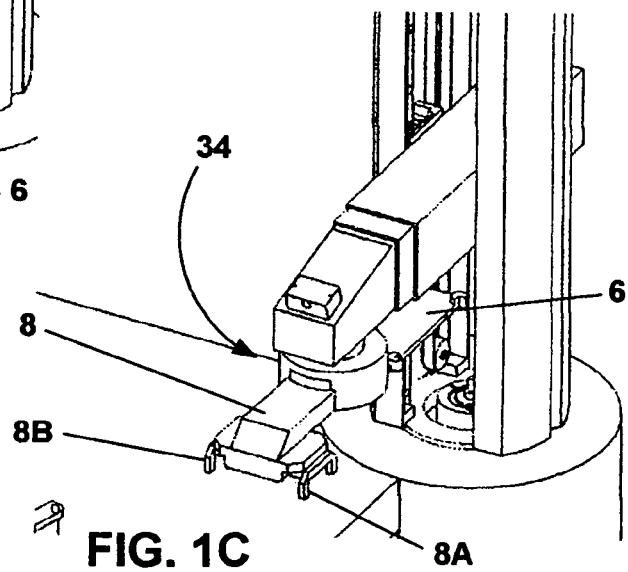
Figure 1D:
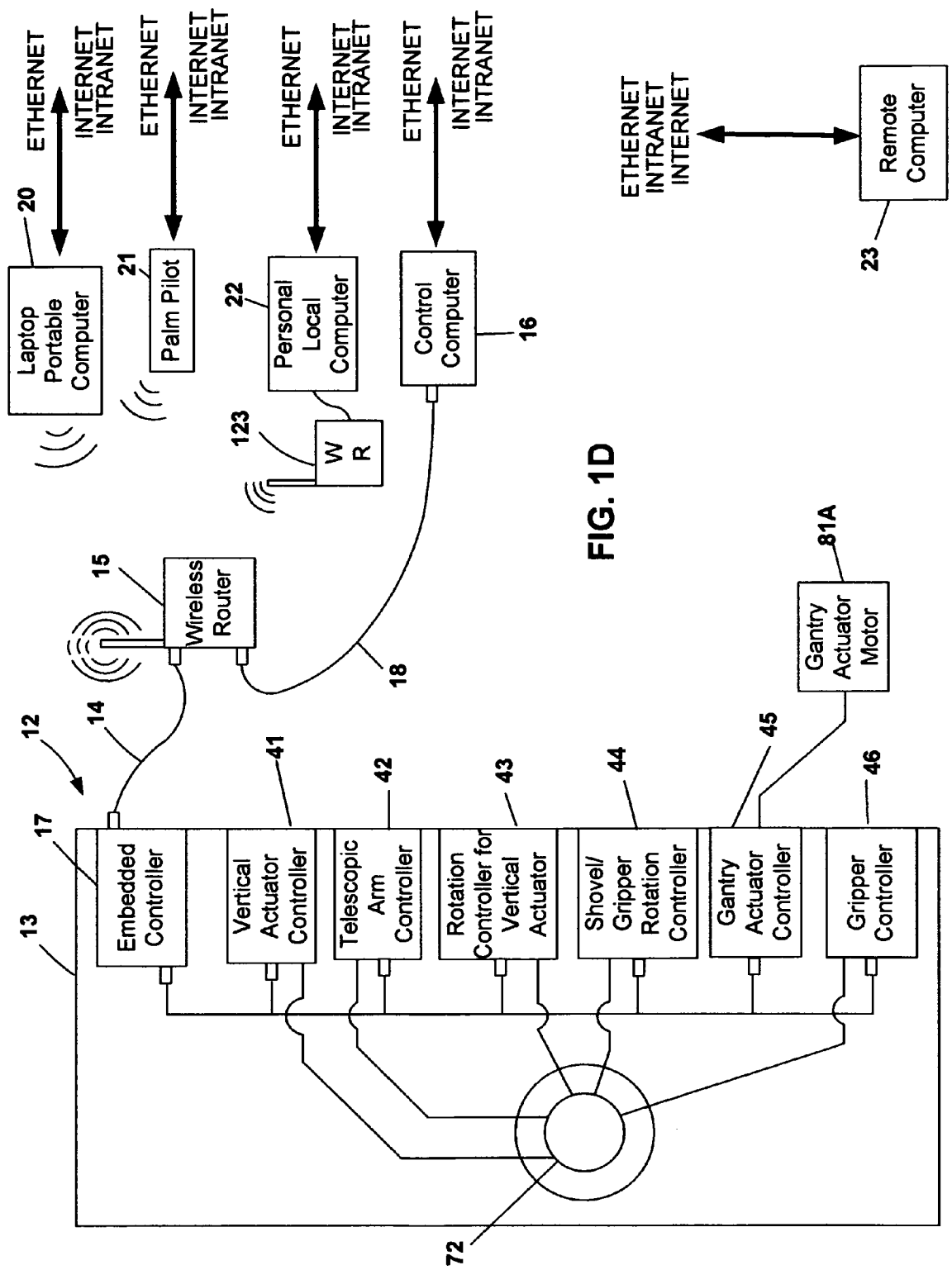

FIGS. 1D and 1E show preferred mechanisms and connectivity for controlling micro-well plate handling robot 12.

Wireless Control

Wireless router 15 is connected to embedded controller 17 via cable 14. Embedded controller 17, embedded inside base 13 of robot 12, controls the mechanisms and components of robot 12. Various types of wireless control devices communicate control signals via wireless router 15. In a preferred embodiment, wireless router 15 is capable of receiving RF signals, infrared signals, free space laser signals and a variety of other wireless signals according to IEEE 802.11b and IEEE 802.11g (2.4 GHz) standards. For example, FIG. 1D shows portable laptop computer 20, palm pilot 21 and personal computer 22 (in wireless communication with wireless router 123) all transmitting control signals to wireless router 15.

Wire Control

Robot 12 can also be controlled via wire connectivity. For example, as shown in FIG. 1D, control computer 16 is connected to a LAN (in this case, the Intranet). Control computer 16 has a direct connection to wireless router 15 via cable 18.

Computer Network Control

As shown in FIG. 1D, robot 12 can also be controlled through a computer network. In FIG. 1D, remote computer 23 is connected to an Ethernet, the Internet and/or an Intranet. Control computer 16 may be connected to an Ethernet, the Internet and/or an Intranet. Hence, control signals sent from remote computer 23 are sent through Ethernet, Internet or Intranet networks to wireless router 15. The control signals are then transmitted to embedded controller 17 via cable 18.

Embedded Controller

Embedded controller 17 is preferably a Windows CE.NET based controller. Because embedded controller 17 preferably has its own embedded web server and its own web site installed, the control computers do not need to have special software installed to control robot 12. Any computer with access to embedded controller 17 can access its website and control robot 12.

Embedded controller 17 receives control signal inputs from various control computers, as described above. Based on the control signals, embedded controller 17 sends control instructions to control cards 41-46.

Vertical Linear Actuator

Vertical Linear Actuator 4 is shown in FIG. 1A and FIG. 1E. In the preferred embodiment linear actuator 4 is a belt-driven linear actuator. Motor 50 (see also FIG. 2) is mounted to the side of linear actuator 4 and drives the belt system in order to raise and lower telescopic gripper arm 5.

Telescopic Gripper Arm

Telescopic gripper arm 5 is capable of telescoping outward to increase its length and inward to decrease its length. Telescopic gripper arm is controlled by motor 51, shown in FIG. 1E.

Rotatable Shovel/Gripper Assembly

Rotatable Shovel/Gripper Assembly 34 is connected to the bottom of telescopic gripper arm 5 as shown in FIGS. 1A, 1E, 1B, and 1C. Rotatable Shovel/Gripper Assembly 34 is capable of rotating so that shovel 6 is extended outward (FIGS. 1B and 1E) or so that gripper 8 is extended outward (FIG. 1C). Telescopic gripper arm is controlled by motor 52 (FIG. 1E).

FIGS. 1A and 2 through 23 describe a sequence showing the operation of a preferred embodiment of the present invention.

In FIG. 1A, a lab technician has loaded micro-well plate storage unit 2 at station 3A. Micro-well plate storage unit 2 (FIG. 1F) is a micro-well plate storage unit for holding micro-well plates and includes tabs 61 for holding the micro-well plates. For micro-well plate storage unit 2, tabs 61 are spaced approximately 1 inch apart and the bottom tab is approximately ½ inch from the bottom of micro-well plate storage unit 2.

The lab technician accesses control computer 16 located near robot 12. Control computer 16 is connected to embedded controller 17 via a computer network connection as shown in FIG. 1D. As stated above, a website for controlling robot 12 has been programmed into embedded controller 17. The lab technician accesses the website and enters into embedded controller 17 the specifics regarding the placement of micro-well plate storage unit 2 at station 3A. For example, the website loaded on embedded controller 17 is preferably pre-programmed with the possible locations of the micro-well plate storage units and the plate spacing for the different possible micro-well plate storage units. The lab technician then only needs to select which station the micro-well plate storage unit is located at and what type of micro-well plate storage unit is there and the website loaded on embedded controller 17 will automatically calculate the above described measurements for micro-well plate storage unit 2 and tabs 61. Also, preferably, robot 12 includes a sensor to detect micro-well plate presence within a micro-well plate storage unit. Therefore, before any tasks occur, robot 12 would inventory the micro-well plate storage unit so that it knows what plates are available for moving. As shown in FIG. 1A, there are twenty-five micro-well plates stored in micro-well plate storage unit 2 and they are loaded up from the bottom. The top eight holding tabs for micro-well plates are empty.

Figure 23:
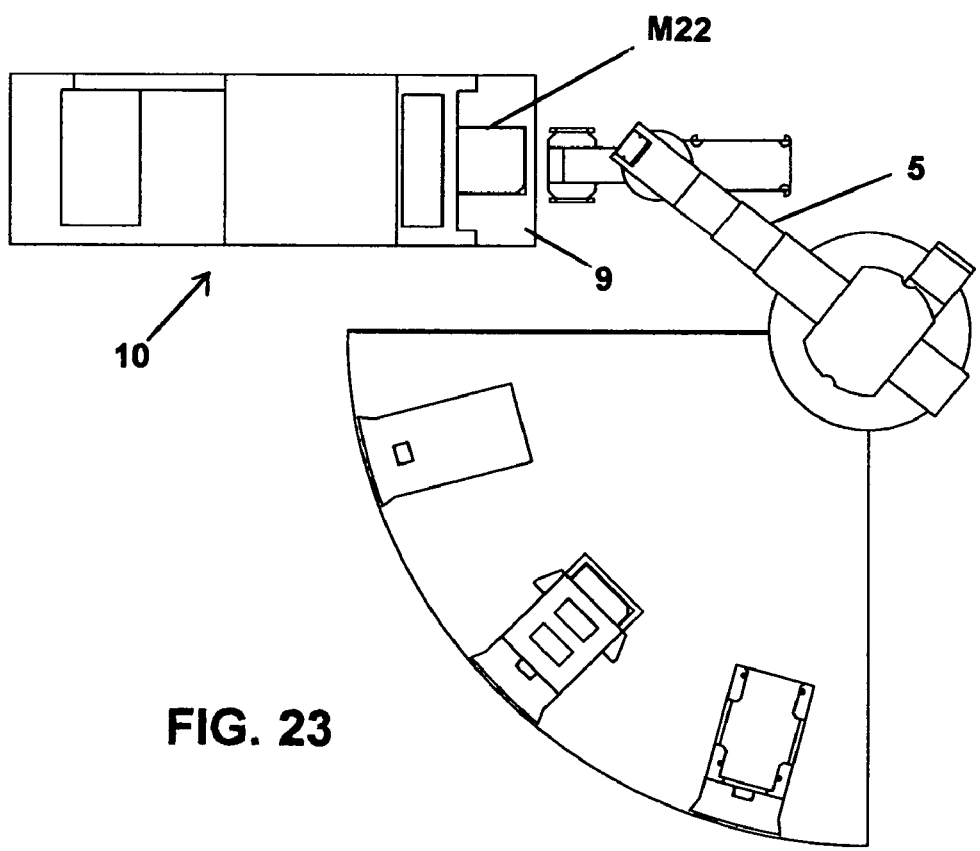

Also, the lab technician enters data that reflects the location and orientation of gripper 8 when it deposits a micro-well plate onto receiving machine 10. For example, when placing a micro-well plate M22 onto platform 9 of receiving machine 10, it is preferable to have the micro-well plate appropriately aligned as shown in FIG. 23. Therefore, the lab technician enters data into embedded controller 17 that reflects the angular orientation relative to robot 12, the distance from robot 12 as well as the vertical height of gripper 8 when it places a micro-well plate onto platform 9. Preferably, gripper 8 location and orientation data is entered via control computer 16 (FIG. 1D). By interfacing with robot 12 via control computer 16, the lab technician maneuvers gripper 8 so that it is located over platform 9 at the position gripper 8 should be when it places a micro-well plate on platform 9. Once robot 12 is at the correct position so that gripper 8 is properly located and oriented over platform 9, the lab technician saves this location in embedded controller 17.

Therefore, after the technician's entry, embedded controller 17 includes data that reflects the location of each of the twenty-five micro-well plates in micro-well plate storage unit 2. Also, embedded controller has entered into it data that reflects the location and orientation gripper 8 should be when it places a micro-well plate on platform 9.

After the specific data regarding micro-well plate storage unit placement, micro-well plate location and the position gripper 8 should be in when it places a micro-well plate on platform 9 are entered into embedded controller 17, a user at remote location logs onto remote computer 23 (FIG. 1D). Remote computer 23 is connected to the Internet as is personal local computer 22. Personal local computer 22 is in communication with embedded controller 17 via wireless router 123 and wireless router 15. Due to the connectivity signal flow from remote computer 23 to personal local computer 22, then to embedded controller 17, the user at remote computer 23 is able to access the website loaded onto embedded controller 17 through a LAN or WAN and control robot 12.

In the sequence described below, the user sends instructions from remote computer 23 to embedded controller 17 to remove micro-well plate M22 (FIG. 1G) from micro-well plate storage unit 2 and place it on platform 9 of receiving machine 10.

Figure 2:
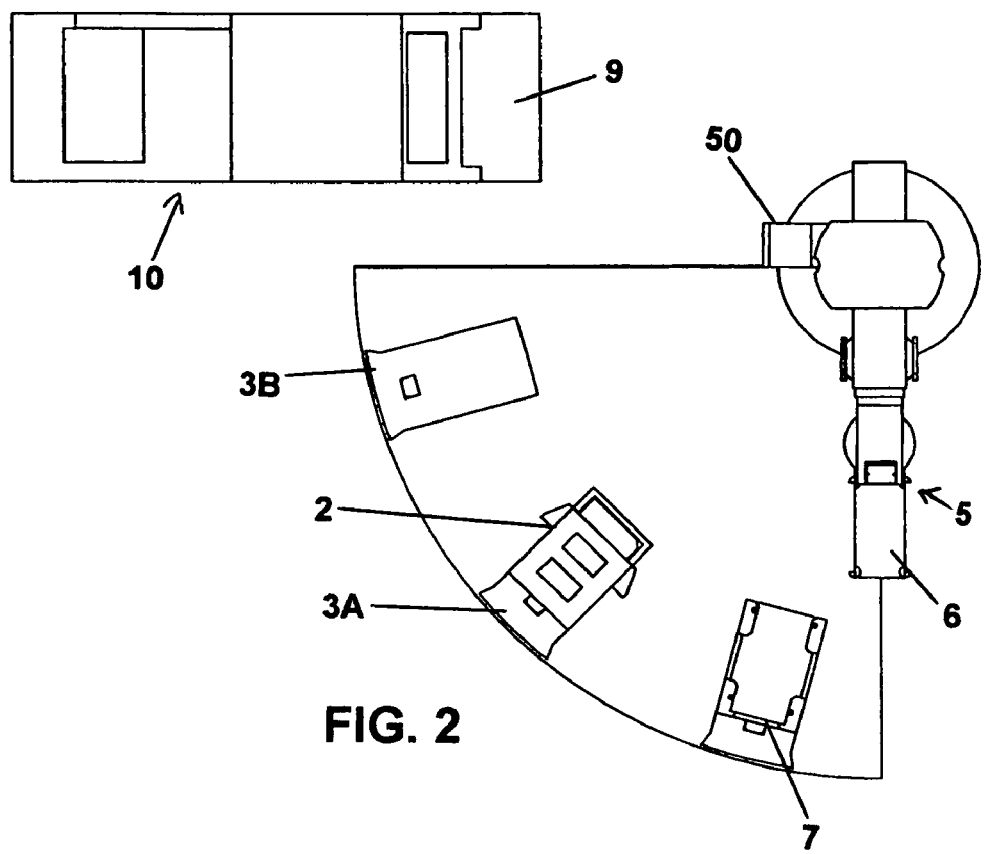
FIGS. 2-23 show a sequence illustrating the operation of the first preferred embodiment.

FIG. 2 is a top view of the image shown in FIG. 1A. In FIG. 2, telescopic gripper arm 5 is in the same position shown in FIG. 1A. Micro-well plate storage unit 2 is positioned at station 3A and there is no micro-well plate storage unit at station 3B.

Figure 3:
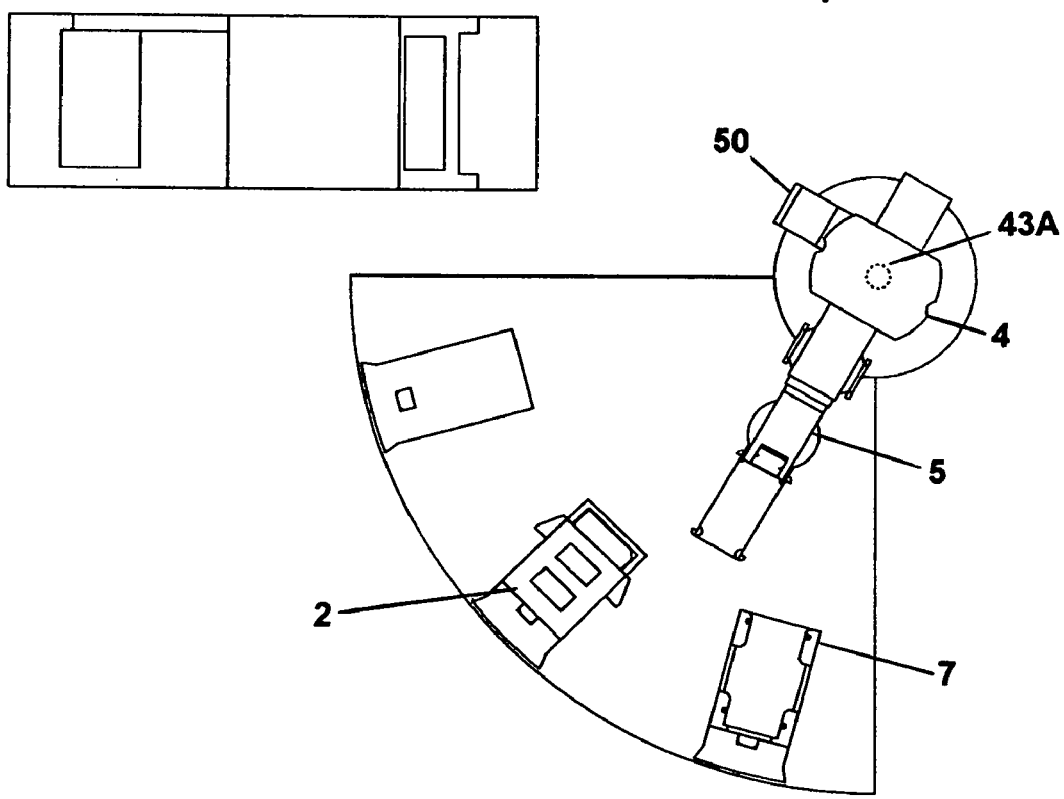

In FIG. 3 vertical actuator rotation controller 43 has sent a signal to motor 43A (FIG. 1E). Motor 43A controls the rotation of shaft 43B. Belt 43C is wrapped around shaft 43B and around belt drive 43D. Belt drive 43D is connected to shaft 43E. Linear actuator 4 is rigidly connected to shaft 43E. Linear actuator 4 rides on and is supported by bearings 43F and 43G. When motor 43A turns shaft 43B, linear actuator 4 rotates about shaft 43E (see also FIG. 3). Hence, in FIG. 3 motor 43A has turned shaft 43B causing linear actuator 4 to rotate about shaft 43E so that telescopic gripper arm 5 is positioned between transfer station 7 and micro-well plate storage unit 2.

Figure 4:
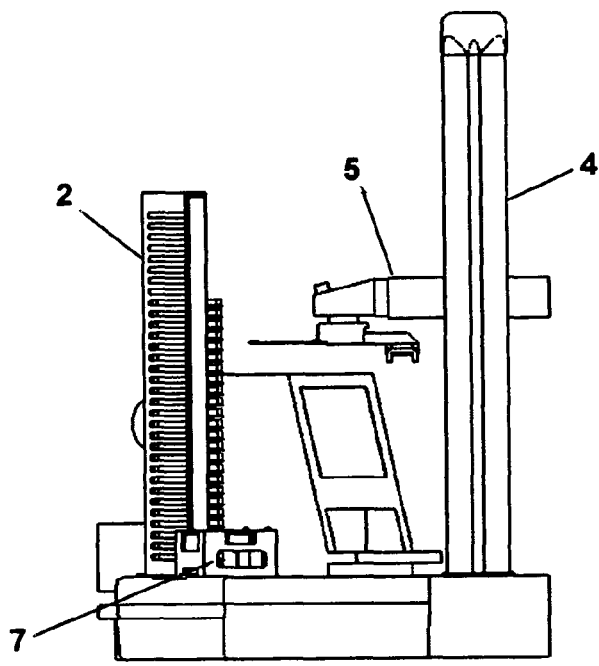

FIG. 4 shows a side view of the image shown in FIG. 3.

Figure 5:
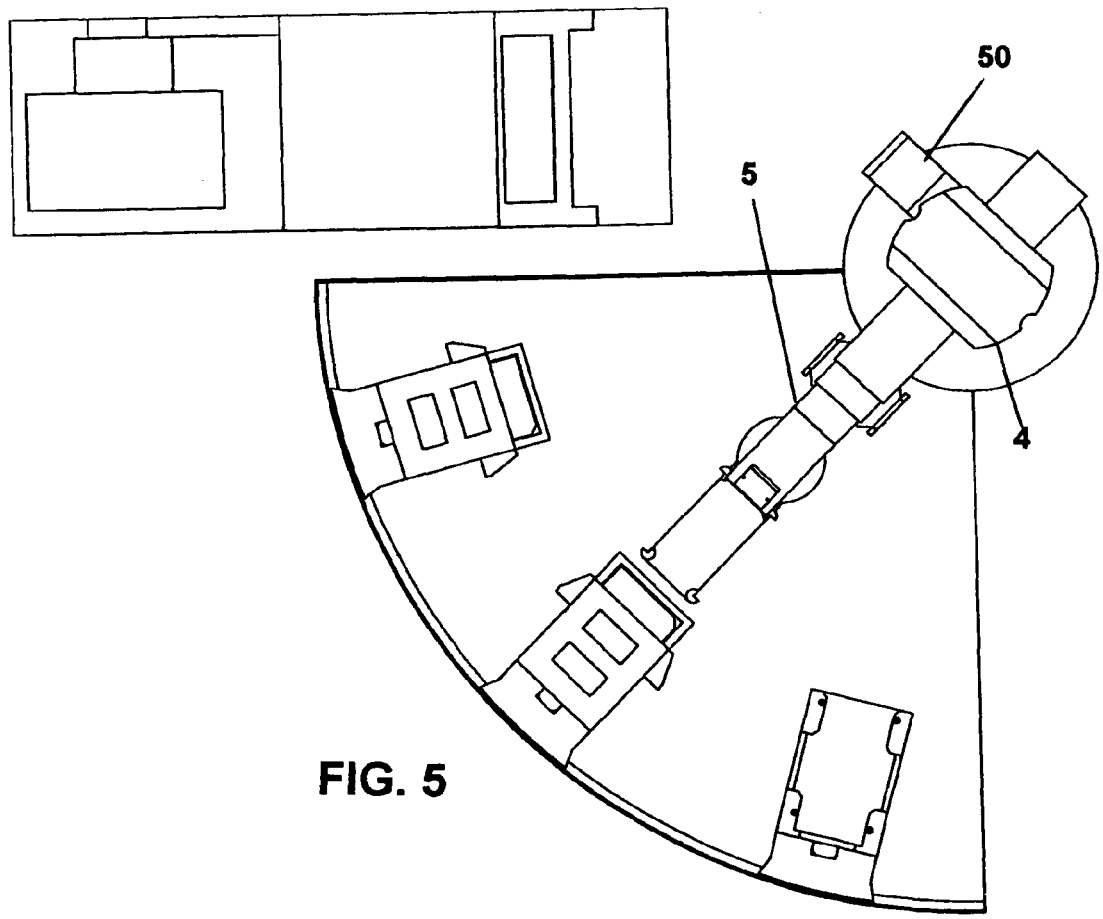

In FIG. 5 motor 43A has continued turning shaft 43B causing linear actuator 4 to rotate so that telescopic gripper arm 5 is positioned in front of micro-well plate storage unit 2. Motor 50 on the side of linear actuator 4 (FIG. 1E, FIG. 3) has raised telescopic gripper arm 5 so that it is at the appropriate height to slide under micro-well plate M22. The height of micro-well plate M22 was preprogrammed into embedded controller 17 (see above discussion). To raise and lower telescopic gripper arm 5, embedded controller 17 sends a control signal to vertical actuator controller 41 (FIGS. 1E, 1H) which in turn sends a control signal to motor 50 via slip ring 72. A preferred slip ring is available from MOOG Inc., with offices in East Aurora, N.Y. Motor 50 controls the turning of shaft 50A (FIG. 1L). Belt 50C is looped around shaft 50A and pulley 50D. Telescopic gripper arm mount 50B is attached to belt 50C and rides on rail 50E. Counterweight 50F is also attached to belt 50C. Telescopic gripper arm 5 is rigidly mounted to telescopic gripper arm mount 50B. As motor 50 turns shaft 50A clockwise (FIG. 1M), telescopic gripper arm 5 is raised. For example, in FIG. 1N, telescopic gripper arm 5 has been raised to the top of linear actuator 4.

Figure 6:
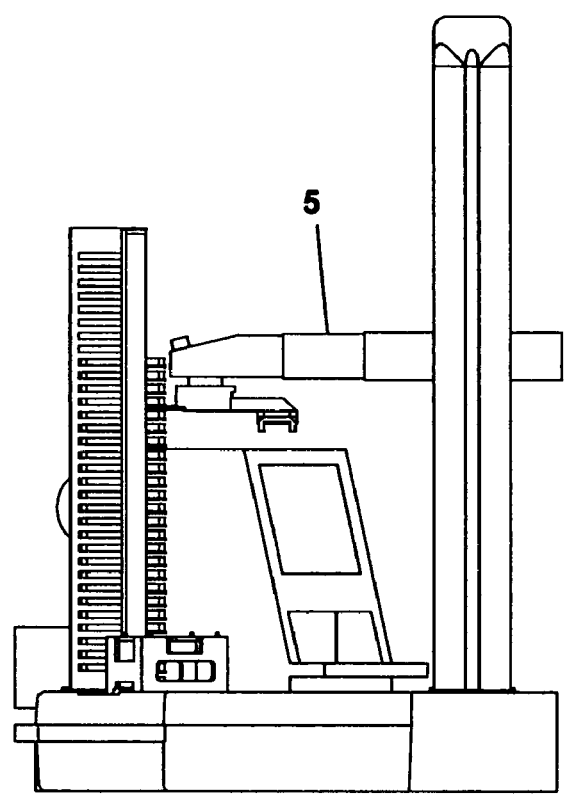
Figure 7:
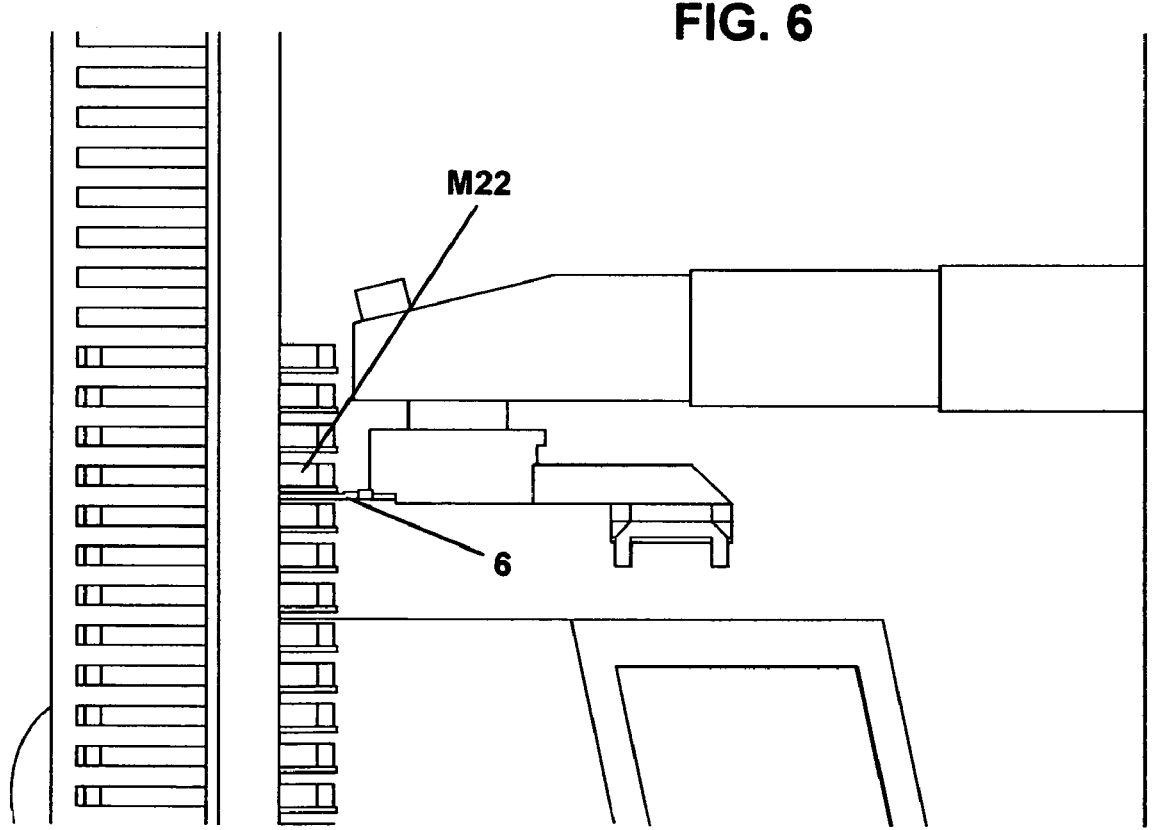

In FIGS. 6 and 7 telescopic gripper arm 5 has extended outward so that shovel 6 is extended under micro-well plate M22. It can be seen that by referring to FIGS. 1F, 1G and 7, tabs 61 of micro-well plate storage unit 2 are spaced such that there are vertical clearance spaces between the micro-well plates vertically stacked in micro-well plate storage unit 2. The vertical clearance spaces are each of sufficient distance so that shovel 6 can slide underneath each individual micro-well plate in micro-well plate storage unit 2.

Figure 1H:
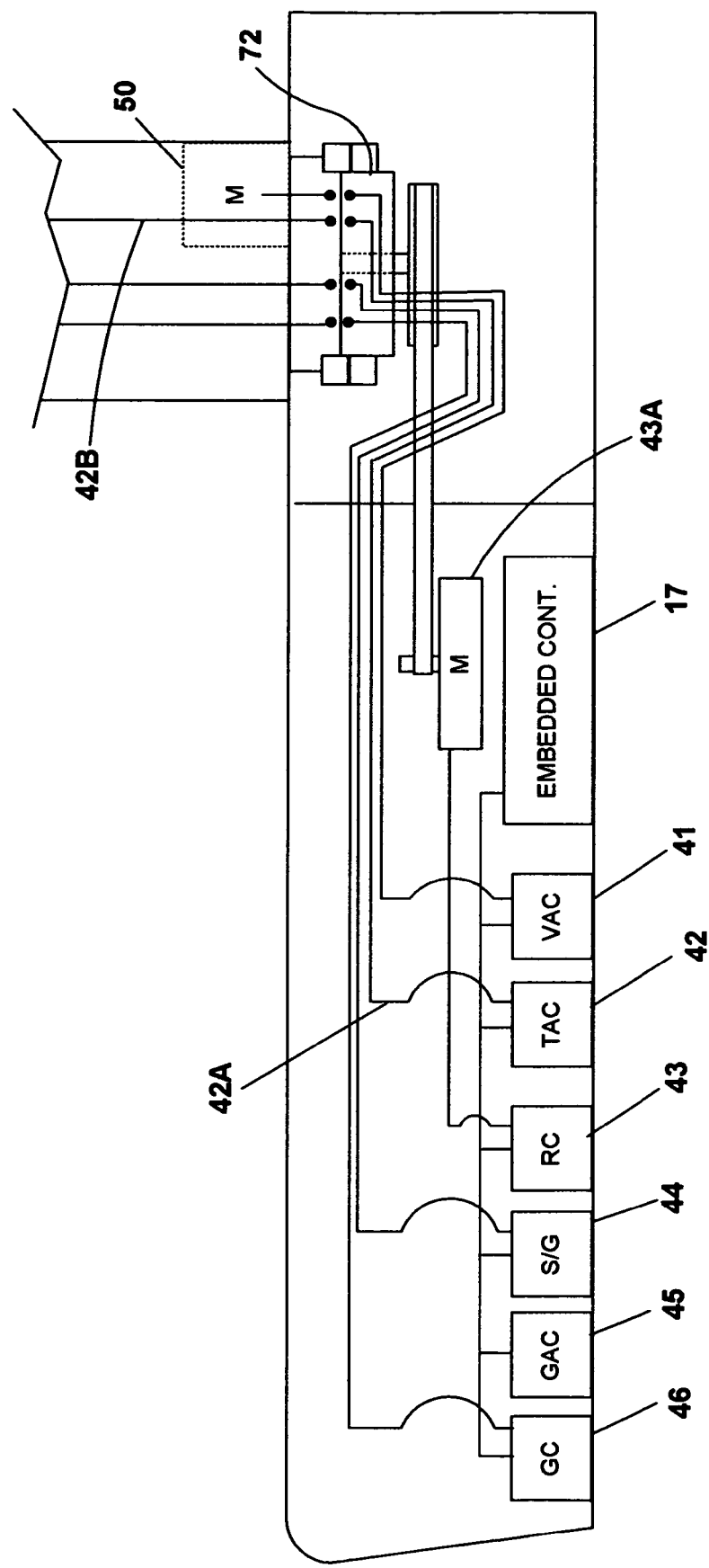
Figure 1N:
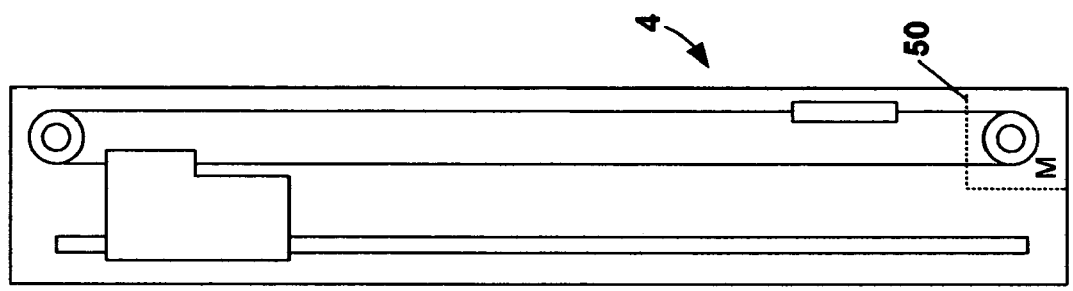
Figure 1M:
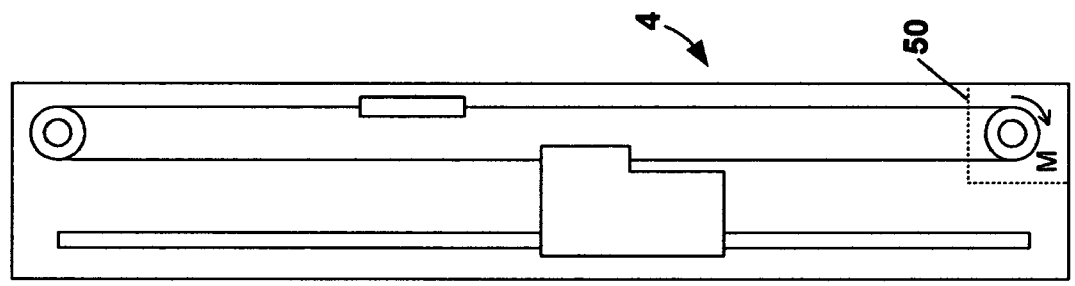
Figure 1L:
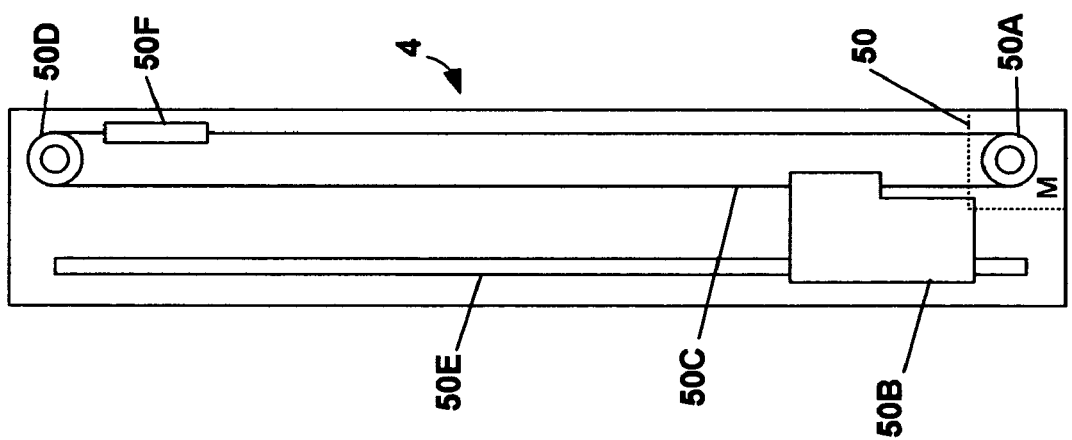

To extend telescopic gripper arm 5, embedded controller 17 sends a control signal to telescopic arm controller 42 (FIGS. 1D, 1E and 1H). Telescopic arm controller 42 sends a control signal through wire 42A to wire 42B via slip ring 72. As shown in FIG. 1H, and as stated above, slip ring 72 allows wire connections to be continuously made between base 13 and linear actuator 4 while linear actuator 4 rotates about shaft 43E. As shown in FIG. 1E, wire 42B transfers the control signal from telescopic arm controller 42 to motor 51.

Motor 51 controls the rotation of shaft 51G of gear 51F (FIG. 1I). Telescopic gripper arm 5 is split into telescopic sections 5A, 5B and 5C. Metallic tape assembly 51B includes metallic tape 51A coiled around spring-loaded spool 51D in a fashion similar to a common tape measure. Spring-loaded spool 51D is loaded to wind metallic tape 51A in a clockwise direction. As with the metallic tape in a tape measure, metallic tape 51 can provide compressive force against section 5A without buckling. Holes 51E have been drilled through metallic tape 5B to coincide with the teeth on gear 51F. In a preferred embodiment, metallic tape assembly 51B is a ¾ inch wide blade tape measure available from Stanley Tools Product Group with offices in New Britain, Conn., part no. 33-012. In FIG. 1I, motor 51 has rotated counterclockwise to extend telescopic gripper arm 5 outward. In FIG. 1J, motor 51 has rotated gear 51F clockwise to retract telescopic gripper arm 5 inward. FIG. 1K shows a perspective view of some of the components of metallic tape assembly 51B.

Figure 8:
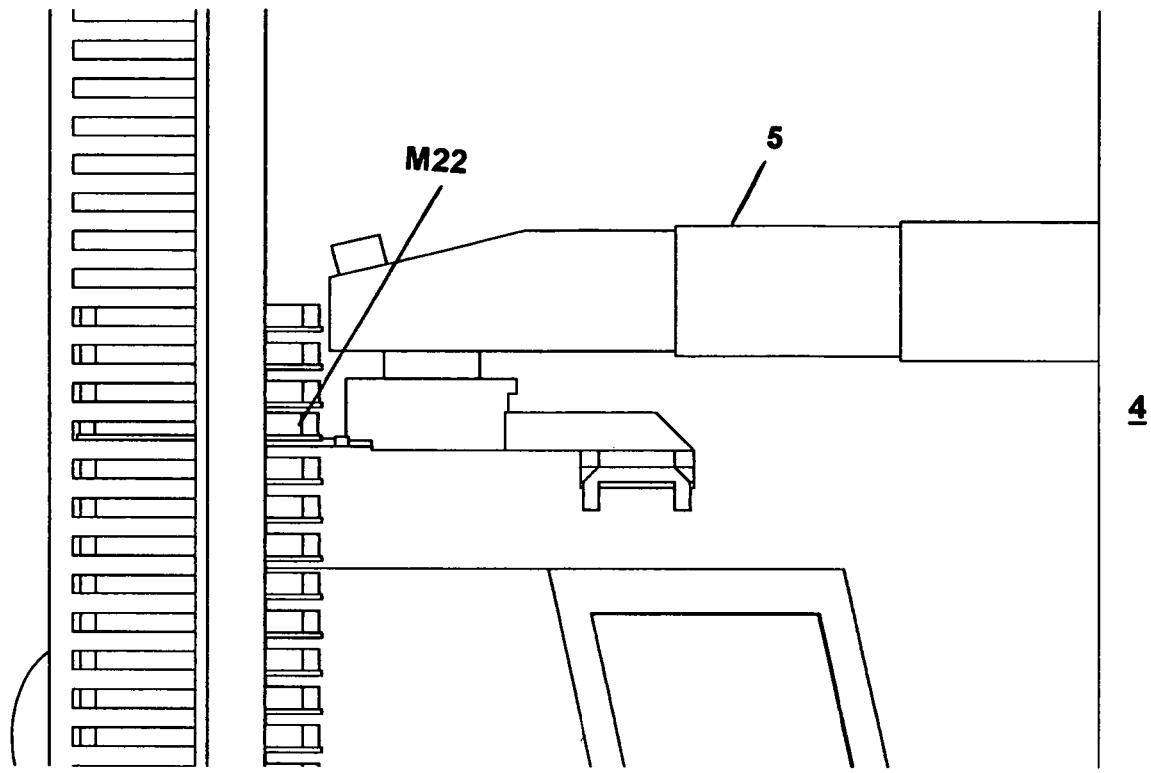

In FIG. 8 motor 50 (FIG. 1L) has caused linear actuator 4 to lift telescopic gripper arm 5 so that shovel 6 has lifted micro-well plate M22 upwards, clearing it from tabs 61 (FIG. 1F).

Figure 9:
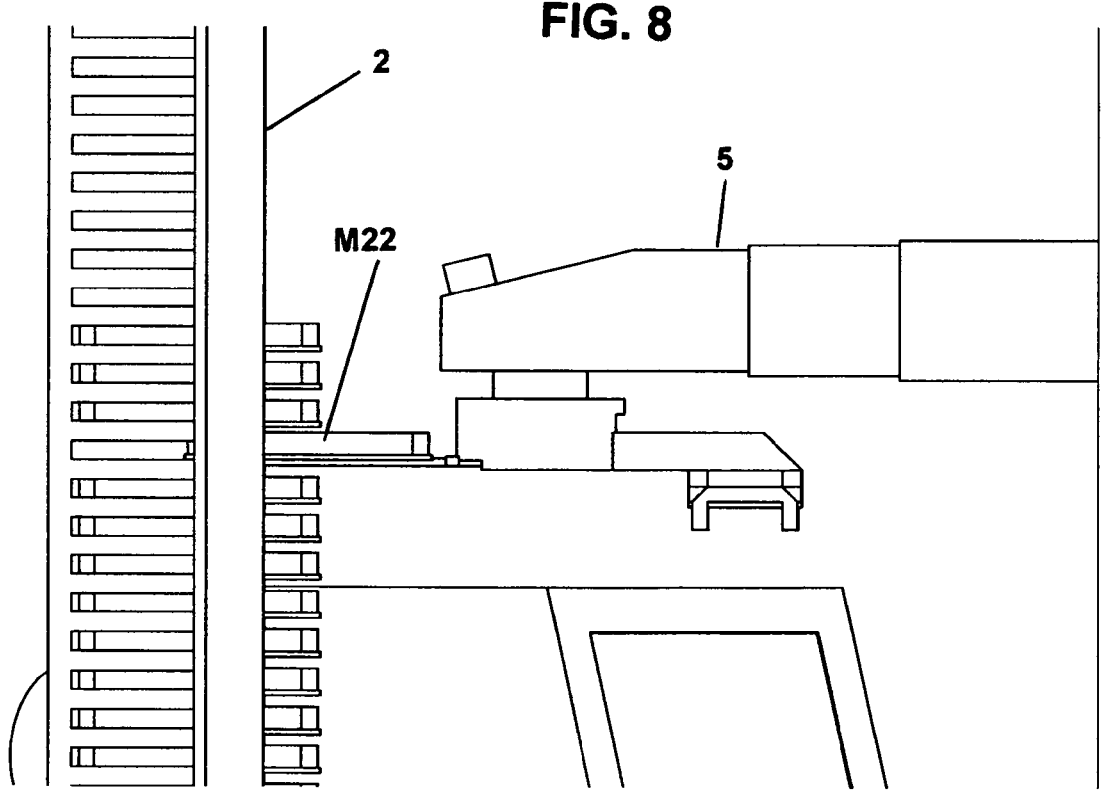

In FIG. 9 motor 51 (FIG. 1I) has rotated gear 51F causing telescopic gripper arm 5 to retract so as to partially remove micro-well plate M22 from micro-well plate storage unit 2.

Figure 10:
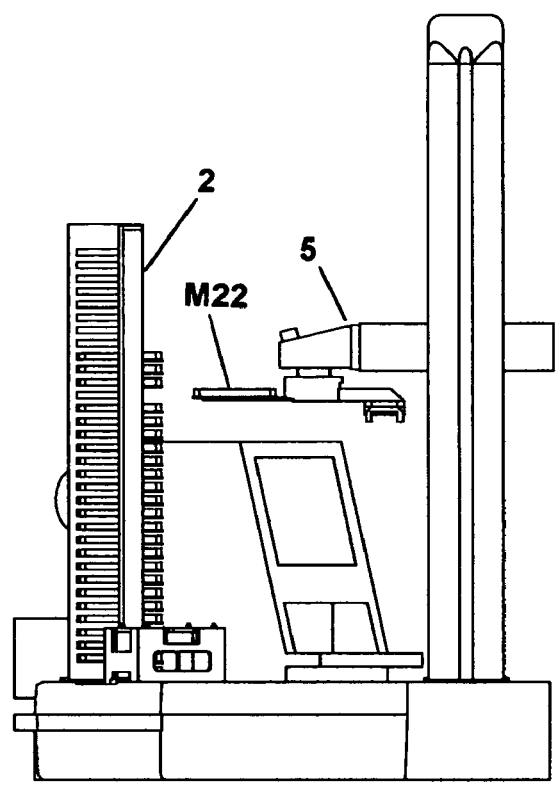

In FIG. 10 motor 51 (FIG. 1I) has rotated gear 51F causing telescopic gripper arm 5 to retract so as to fully remove micro-well plate M22 from micro-well plate storage unit 2.

Figure 11:
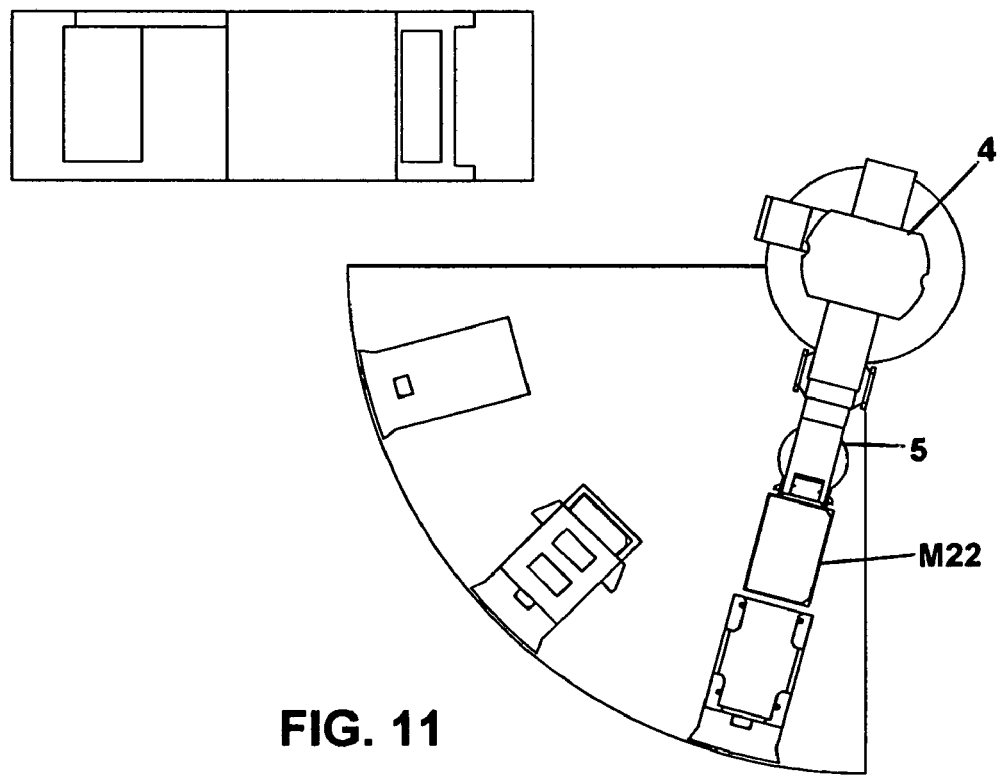

In FIG. 11 motor 43A (FIGS. 1E, 1H) has rotated linear actuator 4 counterclockwise so that telescopic gripper arm 5 is holding micro-well plate M22 in front of transfer station 7.

Figure 12:
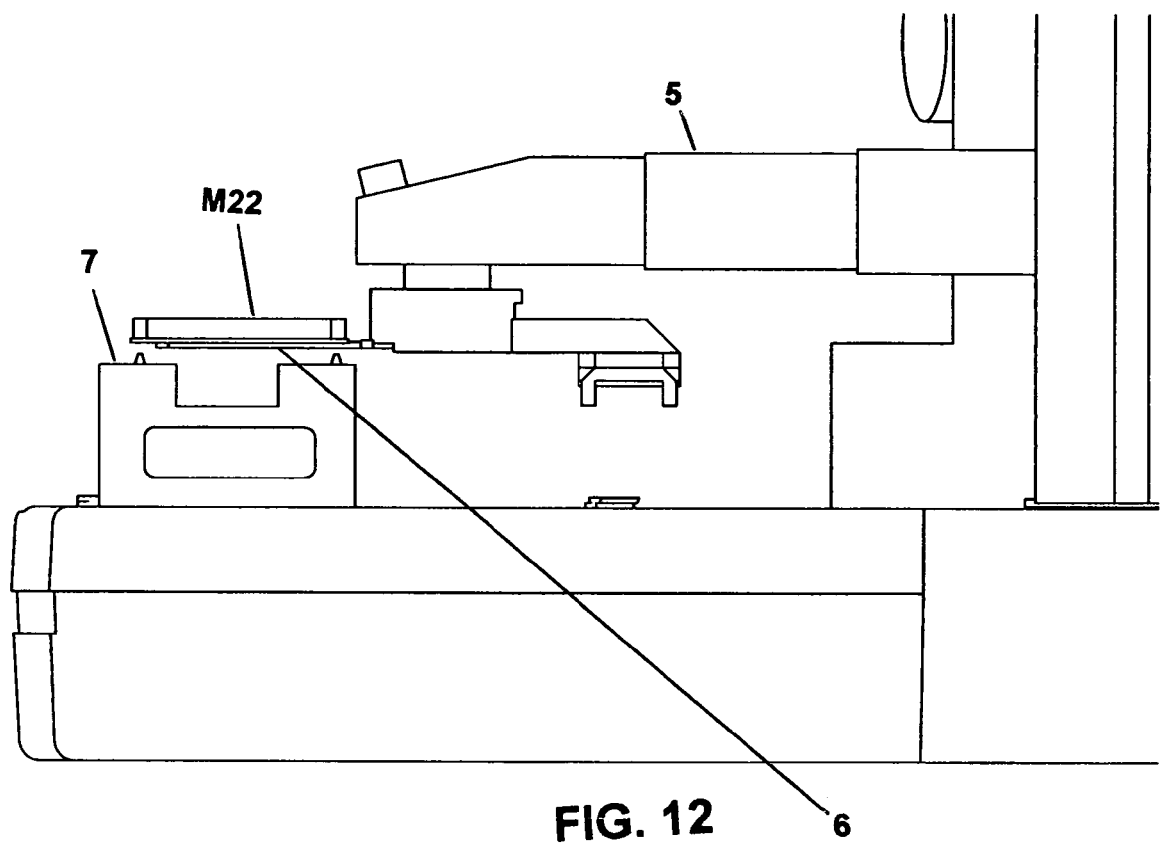
Figure 13:
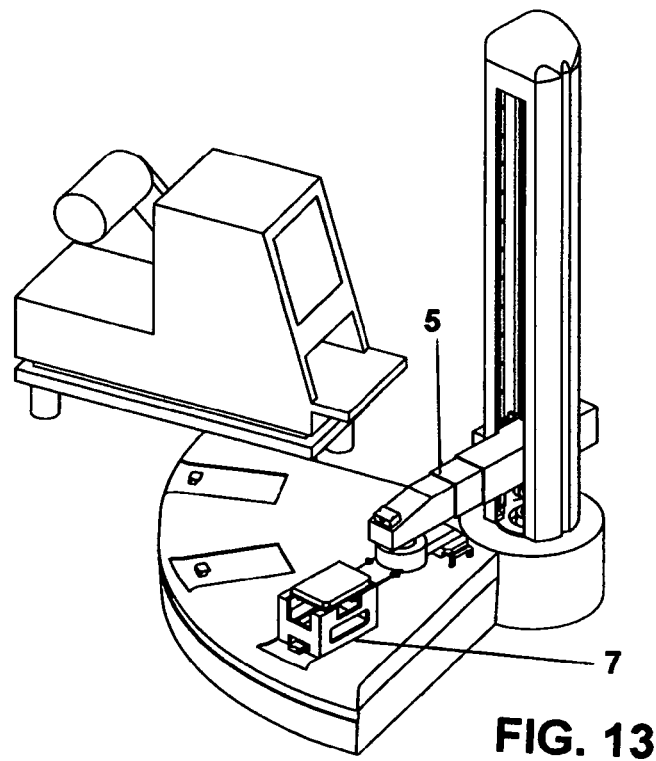

In FIGS. 12 and 13 motor 50 (FIG. 1L) has caused linear actuator 4 to lower telescopic gripper arm 5 so that shovel 6 has placed micro-well plate M22 just above the height of transfer station 7. Also, motor 51 (FIG. 1I) has rotated gear 51F causing telescopic gripper arm 5 to extend so as to place micro-well plate M22 just above transfer station 7.

Figure 14:
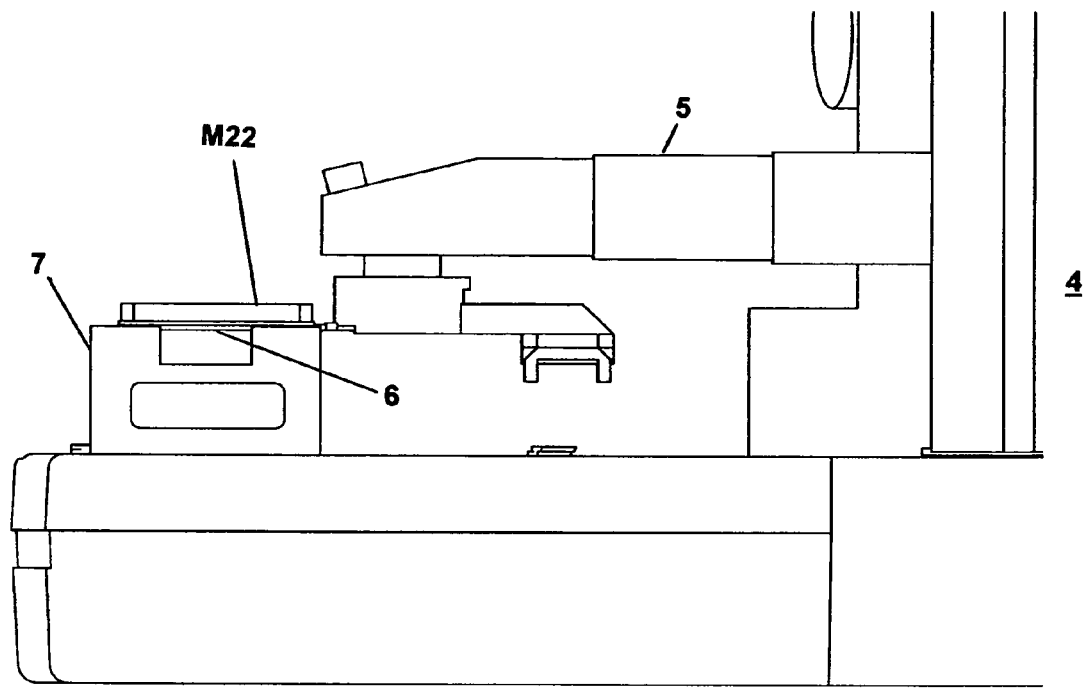

In FIG. 14 motor 50 (FIG. 1L) has caused linear actuator 4 to lower telescopic gripper arm 5 so that shovel 6 has placed micro-well plate M22 on the top of transfer station 7.

Figure 15:
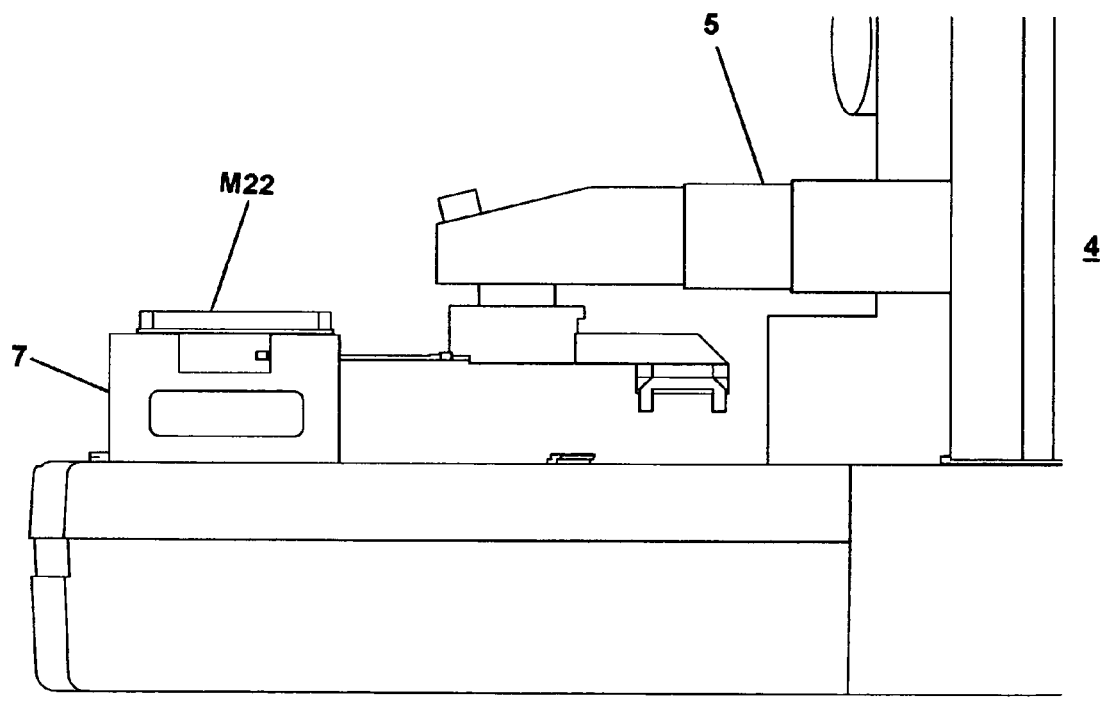

In FIG. 15 motor 50 (FIG. 1L) has caused linear actuator 4 to further lower telescopic gripper arm 5 so that micro-well plate M22 has been left on the top of transfer station 7. Also, motor 51 (FIG. 1I) has rotated gear 51F causing telescopic gripper arm 5 to retract so as to leave micro-well plate M22 on top of transfer station 7.

Figure 16:
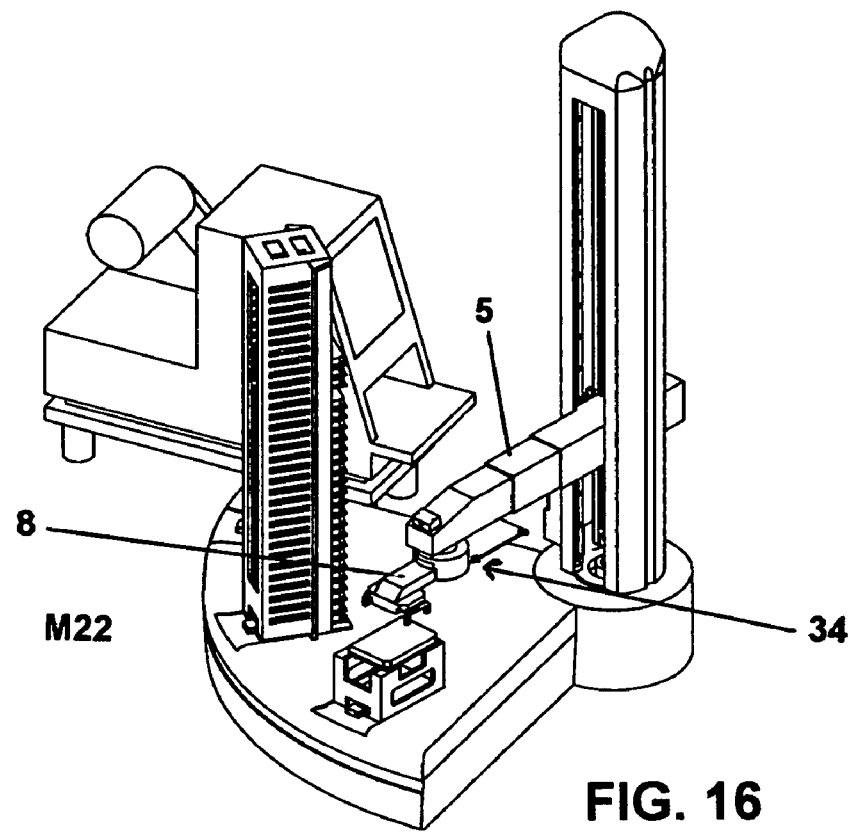

In FIG. 16 motor 52 (FIG. 1E) has rotated rotatable shovel/gripper assembly 34 so that gripper 8 is positioned above micro-well plate M22. Rotatable shovel/gripper assembly 34 is rotatably mounted on the underside of telescopic gripper arm 5 via a shaft controlled by motor 52. To rotate rotatable shovel/gripper assembly 34, embedded controller 17 sends a control signal to shovel/gripper rotation controller 44 which in turn sends a control signal to motor 52 via slip ring 72 (FIGS. 1E, 1H).

Figure 17:
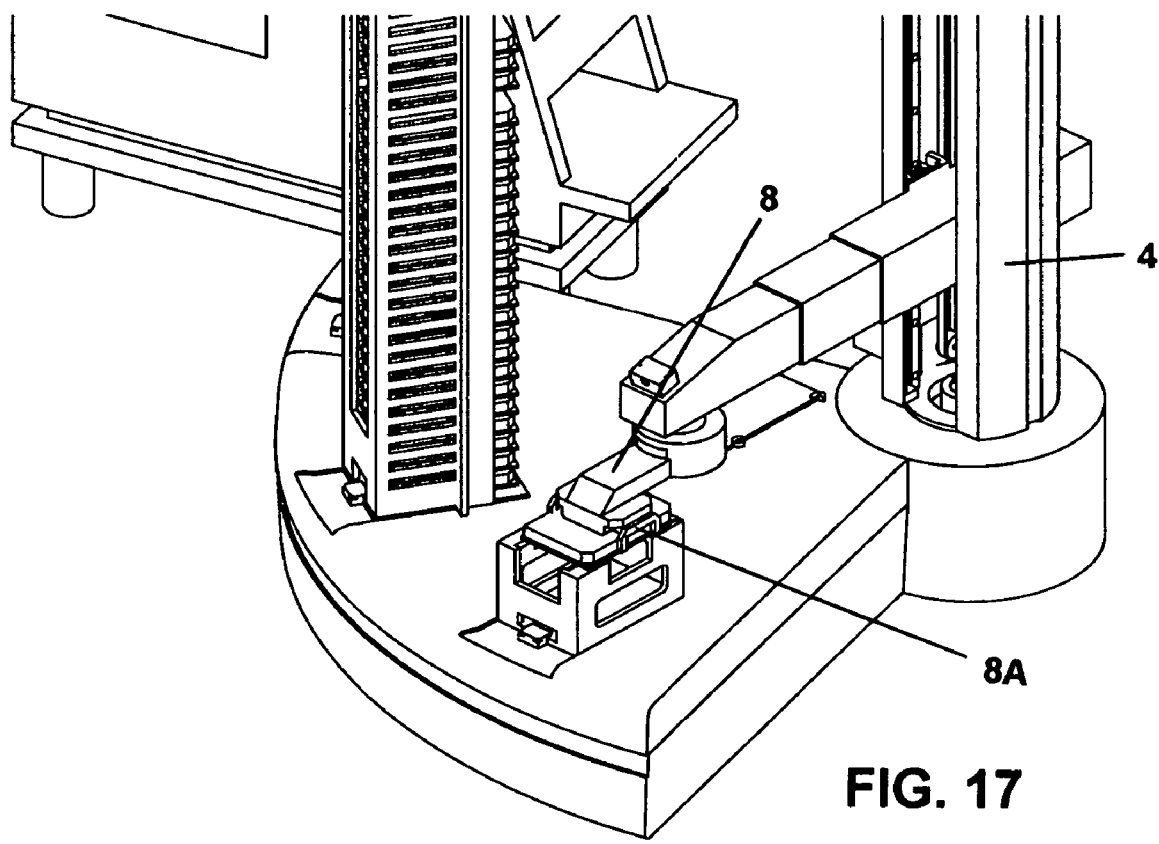

In FIG. 17 motor 50 (FIG. 1L) has caused linear actuator 4 to lower telescopic gripper arm 5 so that gripper 8 has been lowered on top of micro-well plate M22. Motor 53 has activated gripper 8 thereby closing gripper arms 8A and 8B (see also FIG. 1C) tight around micro-well plate M22. To close tightly or loosen gripper arms 8A and 8B of gripper 8, embedded controller 17 sends a control signal to gripper controller 46 which in turn sends a control signal to motor 53 via slip ring 72 (FIGS. 1E, 1H).

Figure 18:
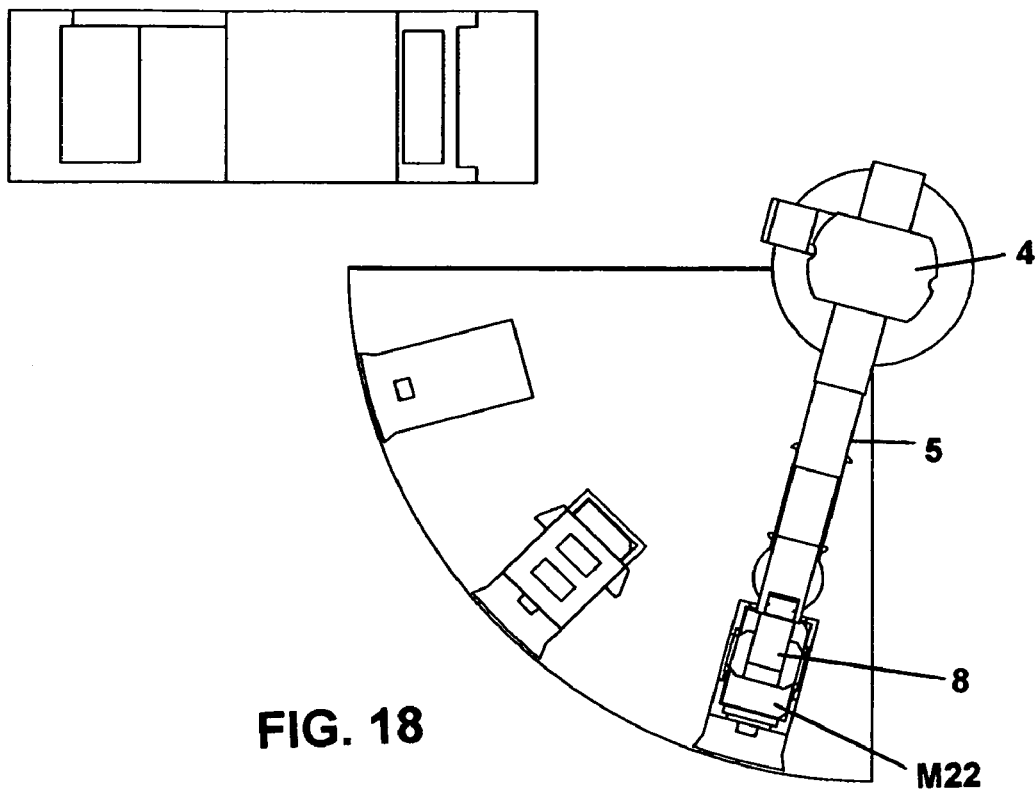

FIG. 18 shows a top view of the image shown in FIG. 17.

Figure 19:
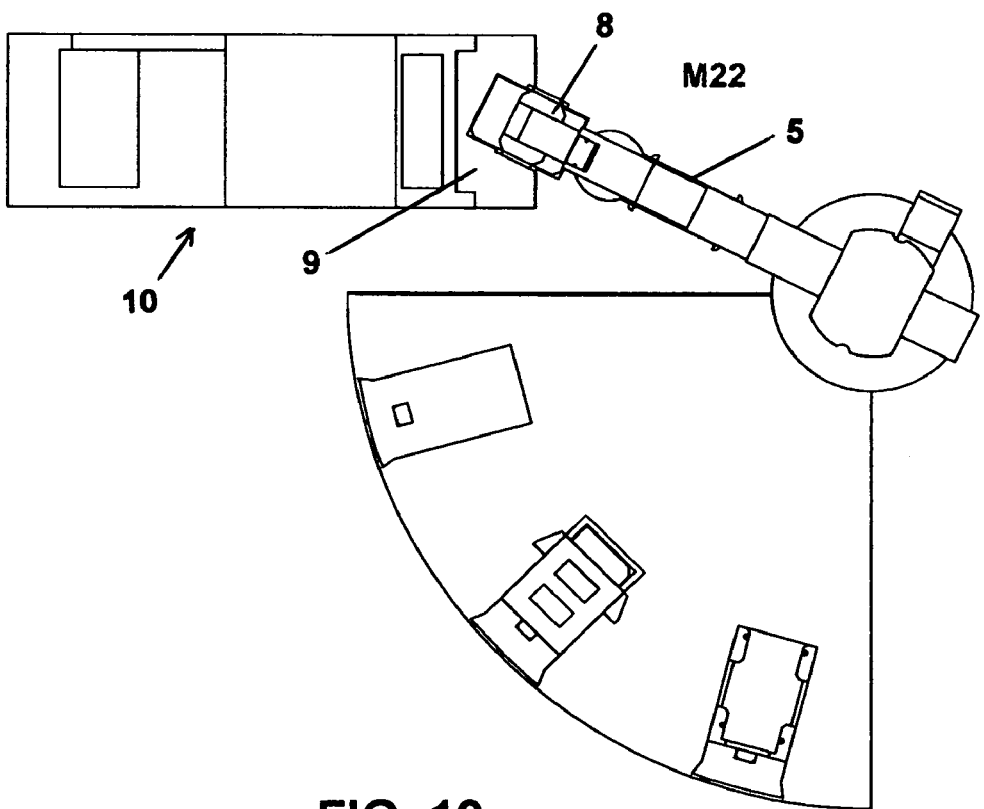
Figure 20:
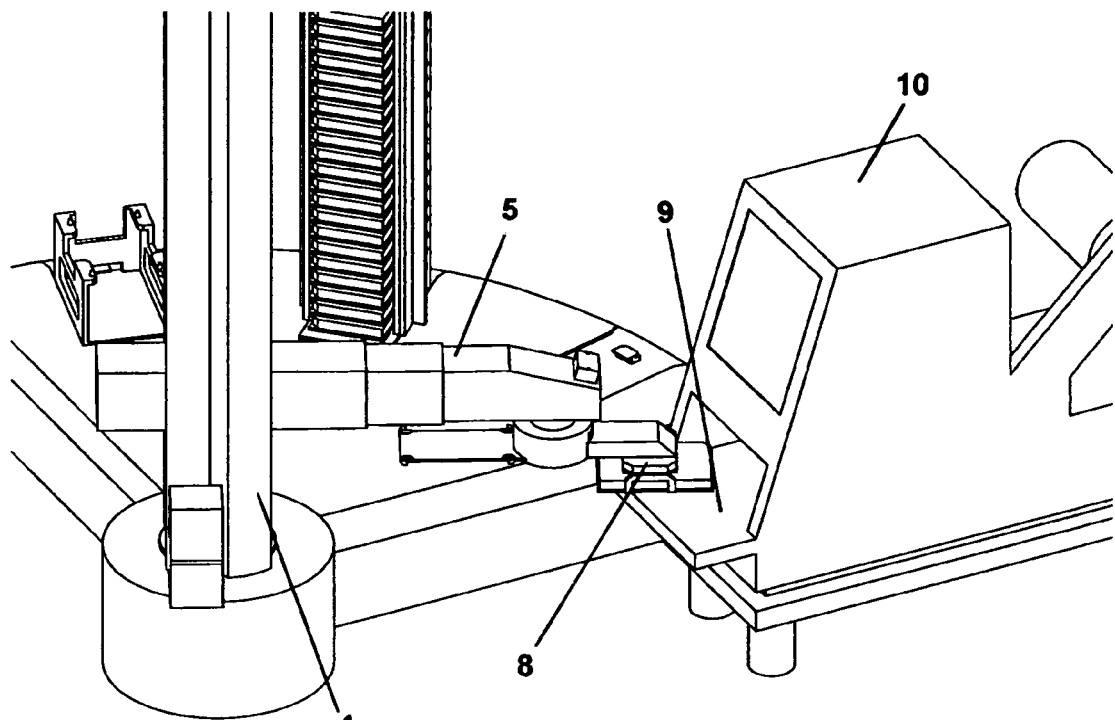

In FIGS. 19 and 20 motor 43A (FIGS. 1E, 1H) has rotated linear actuator 4 clockwise so that telescopic gripper arm 5 is holding micro-well plate M22 over platform 9 of receiving machine 10. Also, motor 50 (see also FIG. 1L) has caused linear actuator 4 to raise telescopic gripper arm 5 so that gripper 8 has placed micro-well plate M22 just above the height of platform 9.

Figure 21:
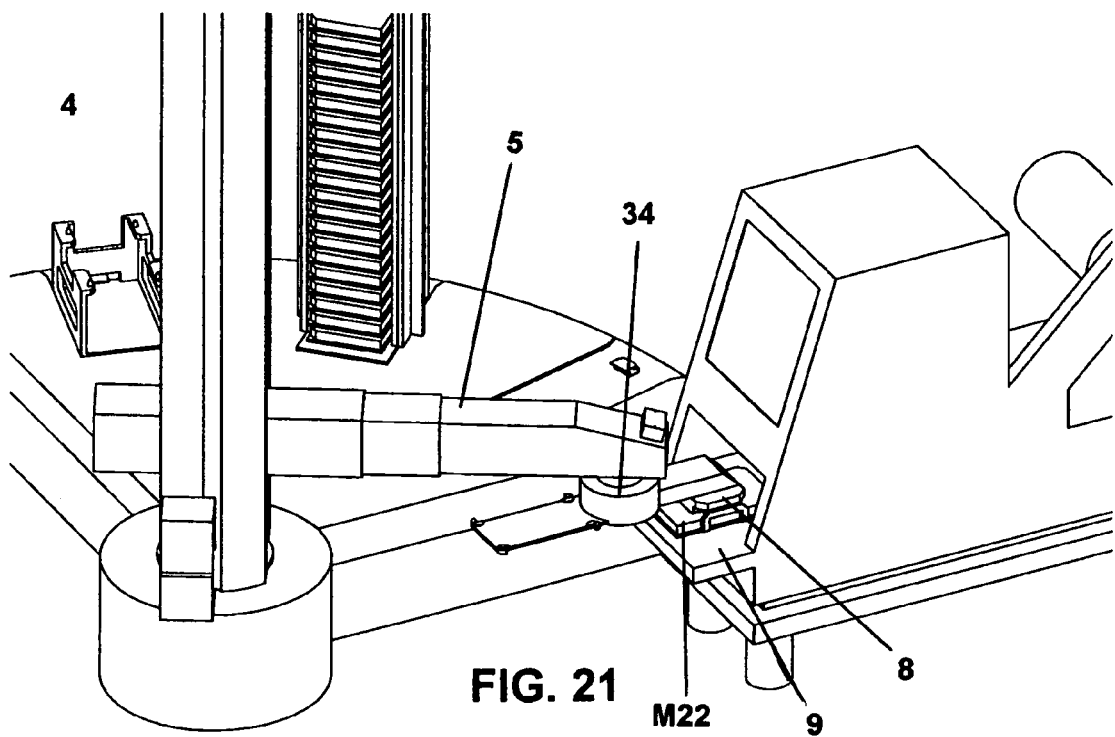
Figure 22:
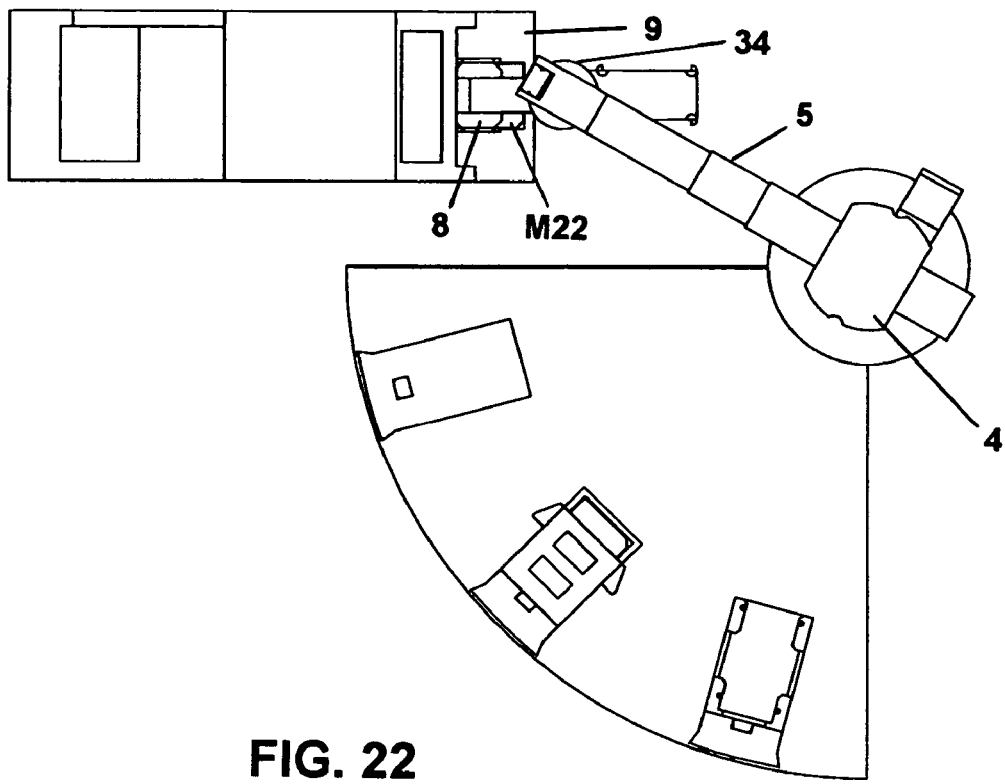

In FIGS. 21 and 22 motor 51 (FIG. 1I) has rotated gear 51F causing telescopic gripper arm 5 to extend slightly. Also, motor 52 (FIG. 1E) has rotated rotatable shovel/gripper assembly 34 counterclockwise so that gripper 8 holding micro-well plate M22 is appropriately orientated with platform 9. As explained above, the orientation, location and height of gripper 8 when it places a micro-well plate on platform 9 were entered into embedded controller 17 by the lab technician. Also, motor 50 (see also FIG. 1L) has caused linear actuator 4 to lower telescopic gripper arm 5 so that the bottom of micro-well plate M22 is in contact with the top of platform 9.

In FIG. 23 motor 53 has activated gripper 8 thereby loosening gripper arms 8A and 8B (see also FIG. 1C) from their hold on micro-well plate M22. Also, motor 51 (FIG. 1I) has rotated gear 51F causing telescopic gripper arm 5 to retract so as to leave micro-well plate M22 on top of platform 9. Micro-well plate M22 has now been left on platform 9, properly orientated so as to be ready for access by receiving machine 10.

After receiving machine 10 is finished with micro-well plate M22, robot 12 will preferably remove micro-well plate M22 from receiving machine 10 and return it to micro-well plate storage unit 2. For example, gripper 8 will be properly positioned and then will grab micro-well plate M22 resting on platform 9. Then linear actuator 4 will lift telescopic gripper arm 5 upward, removing micro-well plate M22 from platform 9. Linear actuator 4 will then rotate counter clockwise so that micro-well plate is positioned in front of transfer station 7. The extension and height of telescopic gripper arm 5 will be adjusted so that micro-well plate M22 is at the appropriate height to be placed on transfer station 7. Gripper 8 will then release its grip on micro-well plate M22, placing it on transfer station 7. Rotatable shovel/gripper assembly 34 is then rotated so shovel 6 is adjacent transfer station 7. The height of shovel 6 is adjusted so that it can be slid under micro-well plate M22 at transfer station 7. Shovel 6 is slid under micro-well plate M22 and is lifted upwards, removing micro-well plat M22 from transfer station 7. Linear actuator 4 is rotated clockwise so that it is positioned in front of micro-well plate storage unit 2. The height of shovel 6 is adjusted so that micro-well plate M22 can be slid into the vacant space in micro-well plate storage unit 2. Shovel 6 is slid into the vacant space in micro-well plate storage unit 2 and lowered so micro-well plate M22 is resting on tabs 61 of micro-well plate storage unit 2. The empty shovel 6 is then retracted from micro-well plate storage unit 2.

Second Preferred Embodiment

Figure 24:
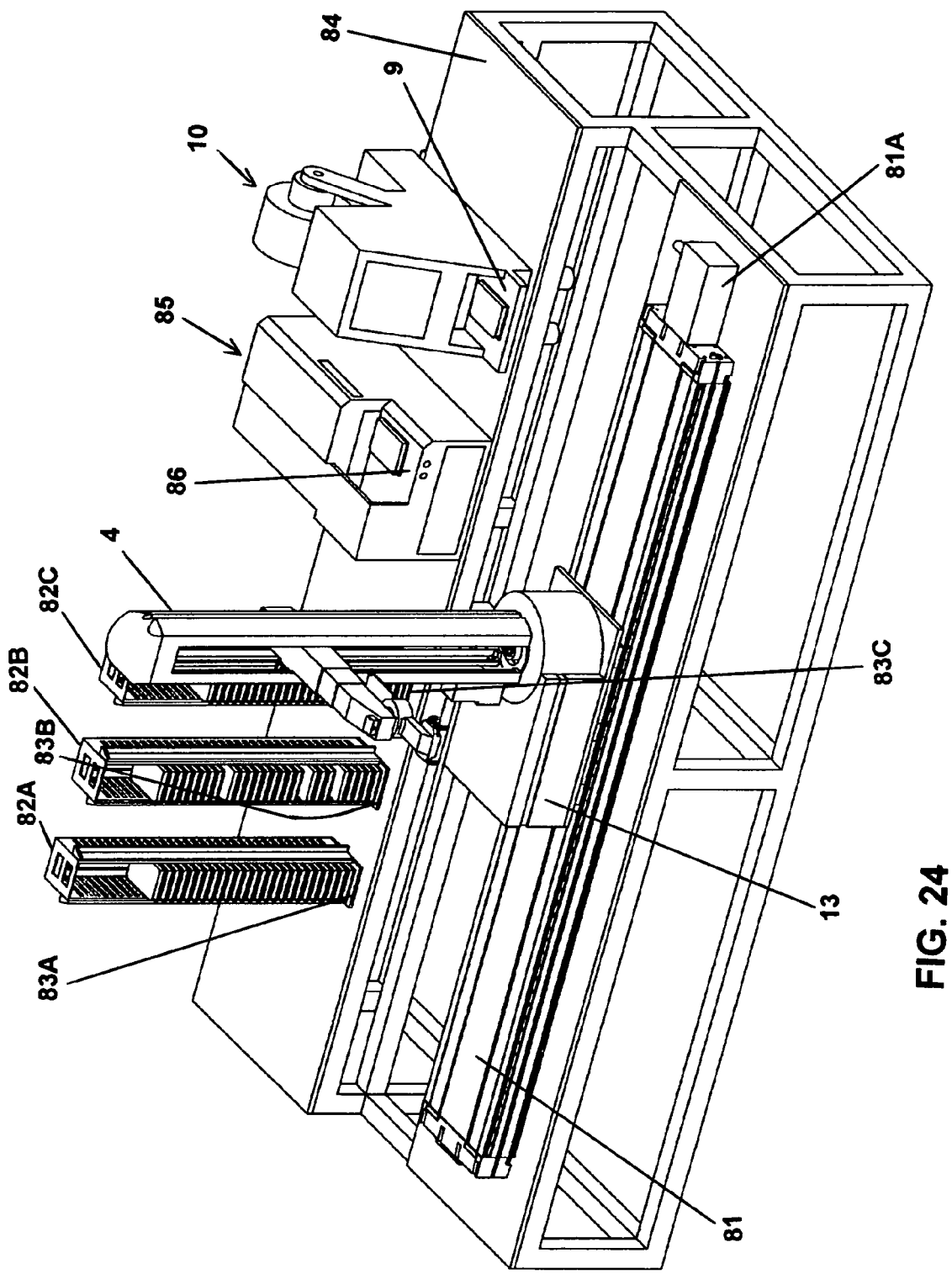
FIG. 24 shows a second preferred embodiment of the present invention.

A second preferred embodiment of the present invention is shown in FIG. 24. Base 13 (FIG. 1E, 1H) with linear actuator 4 is mounted onto gantry 81. Preferably, gantry 81 is a ball screw driven linear actuator that allows for horizontal positioning of linear actuator 4. Gantry 81 is controlled by gantry motor 81A.

Utilization of the Second Preferred Embodiment

As shown in FIG. 24, a lab technician has loaded micro-well plate storage units 82A, 82B and 82C onto stations 83A, 83B, and 83C, respectively, of table 84. Receiving machines 10 and 85 have also been placed on table 84. Due to entries made by the lab technician (see above discussion), the location and orientation of micro-well plate storage units 82A-82C and receiving machines 85 and 10 are entered into embedded controller 17 (FIG. 1E). For example, as shown in FIG. 24, receiving machines 85 and 10 are both arranged so that platforms 86 and 9 have orientations that are aligned with the edge of table 84.

Second Embodiment Sequence

In the following sequence shown in FIGS. 25-32, a user utilizing a portable laptop computer 20 (FIG. 1D) has logged onto the website loaded onto embedded controller 17. After reviewing the website, the user has ascertained that micro-well plate storage units 82A, 82B and 82C are positioned at stations 83A, 83B and 83C respectively. Furthermore, he has ascertained the number and locations of micro-well plates stored in each micro-well plate storage unit. Moreover, he has also ascertained the location of receiving machines 85 and 10.

After reviewing the website, the user enters instructions into embedded controller 17 for the robot to remove micro-well plate M19 from micro-well plate storage unit 82B and place it on platform 9 of receiving machine 10.

Figure 25:
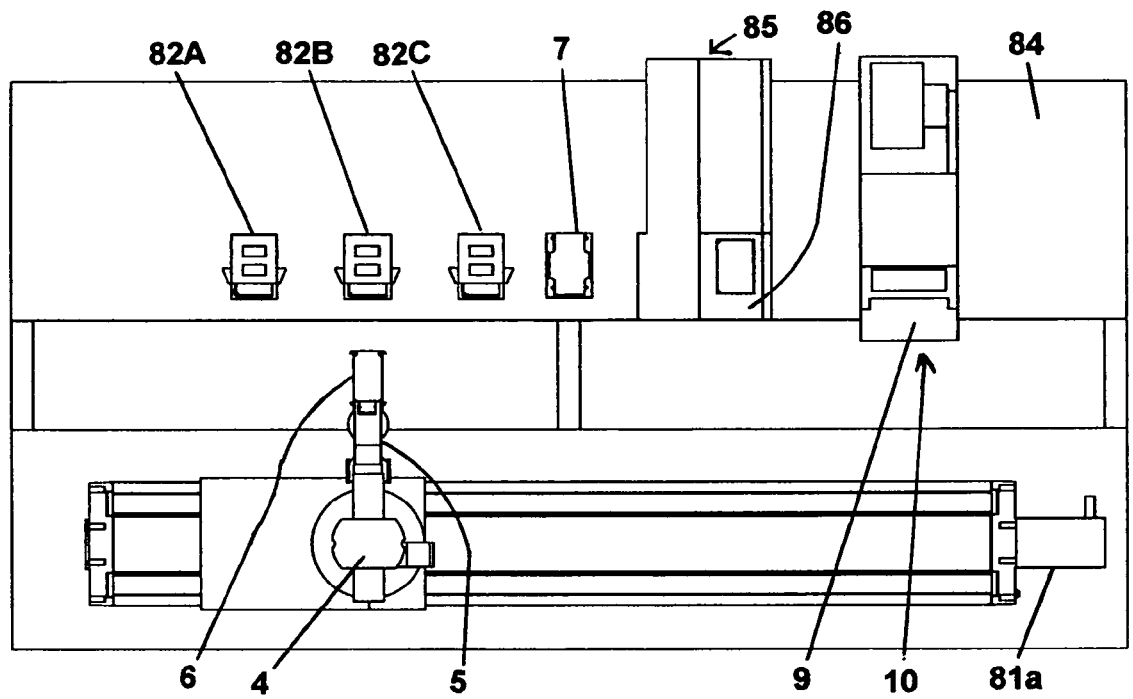
FIGS. 25-32 show a sequence illustrating the operation of the second preferred embodiment.

In FIG. 25, motor 81A has controlled gantry 81 so that it has moved linear actuator 4 so that telescopic gripper arm 5 is positioned in front of micro-well plate storage unit 82B. To control gantry 81, embedded controller 17 sends a control signal to gantry actuator controller 45 which in turn sends a control signal to motor 81A (FIG. 1E). Motor 81A then drives gantry 81 to control the left to right motion of linear actuator 4. Also, in FIG. 25 embedded controller 17 has sent control signals to motor 50 causing linear actuator 4 to raise telescopic gripper arm 5 so that shovel 6 is positioned at the appropriate height to slide under micro-well plate M19.

Figure 26:
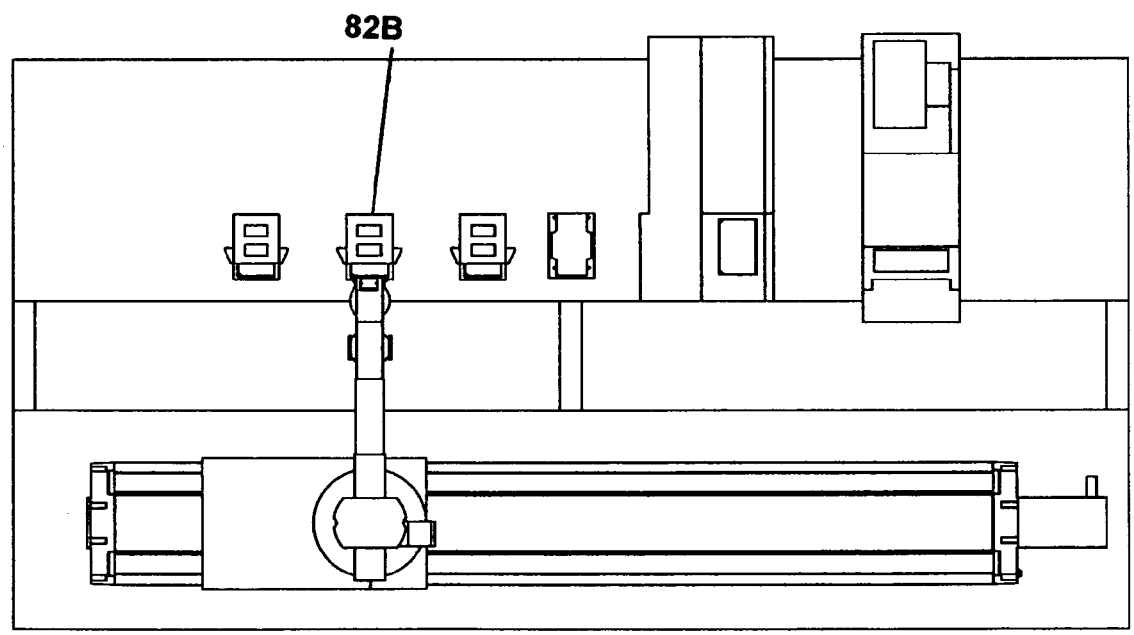

In FIG. 26 motor 51 (FIG. 1I) has rotated gear 51F causing telescopic gripper arm 5 to extend so shovel 6 is inserted into micro-well plate storage unit 82B and underneath micro-well plate M19.

Figure 27:
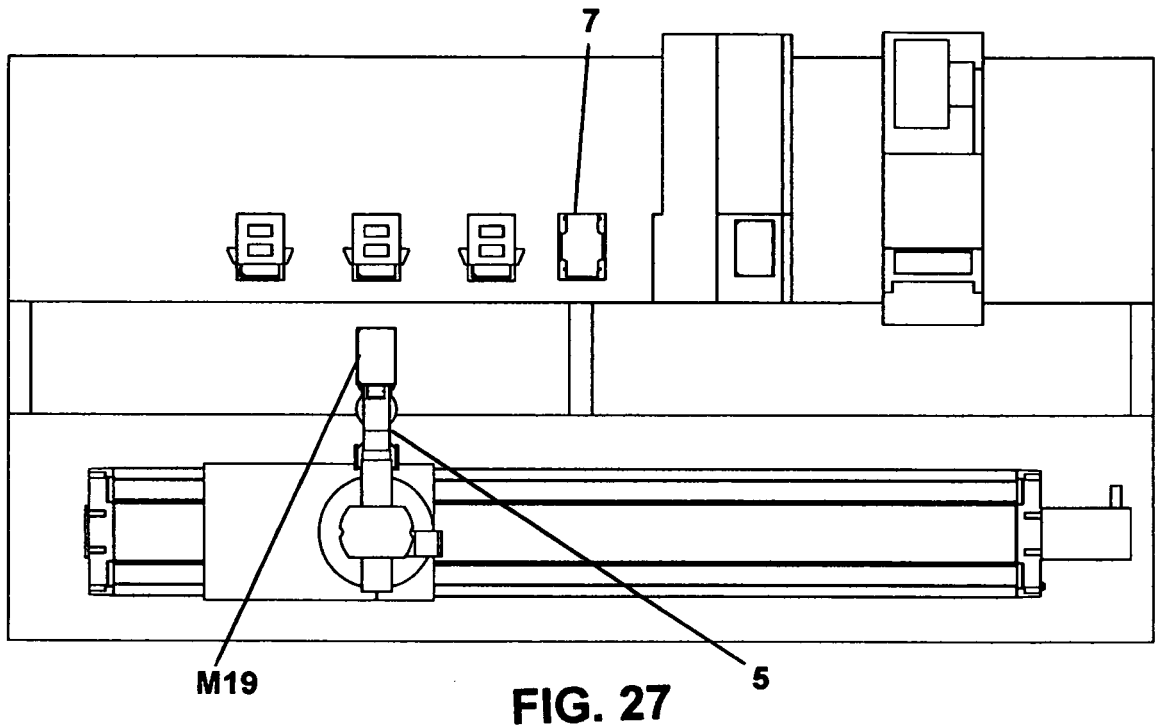

In FIG. 27 motor 50 has caused linear actuator 4 to raise telescopic gripper arm 5 so that shovel 6 has lifted micro-well plate M19 off of tabs 61 (FIG. 1F). Also, motor 51 (FIG. 1I) has rotated gear 51F causing telescopic gripper arm 5 to retract so that micro-well plate M19 has been pulled out of micro-well plate storage unit 82B.

Figure 28:
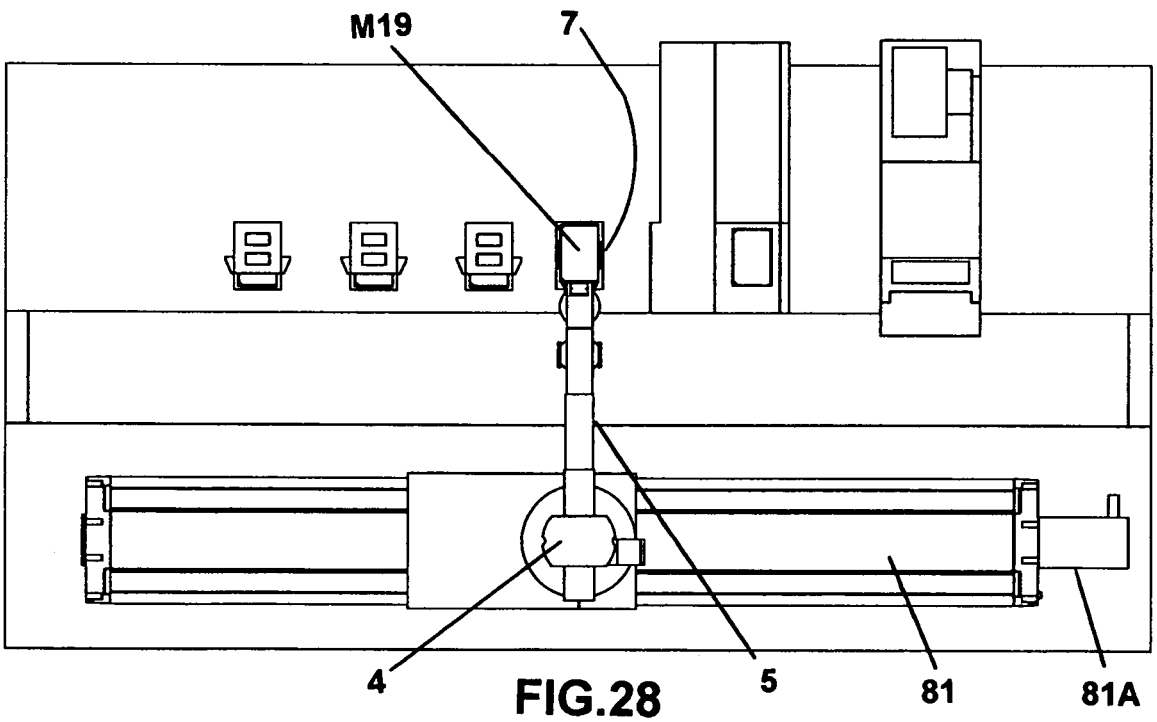

In FIG. 28 motor 81A has controlled gantry 81 so that it has moved linear actuator 4 to the right so that telescopic gripper arm 5 is positioned in front of micro-well plate storage unit transfer station 7. Also, motor 51 (FIG. 1I) has rotated gear 51F causing telescopic gripper arm 5 to extend so that micro-well plate M19 has been placed over transfer station 7. Also, motor 50 has caused linear actuator 4 to lower telescopic gripper arm 5 so that shovel 6 has placed micro-well plate M19 on top of transfer station 7.

Figure 29:
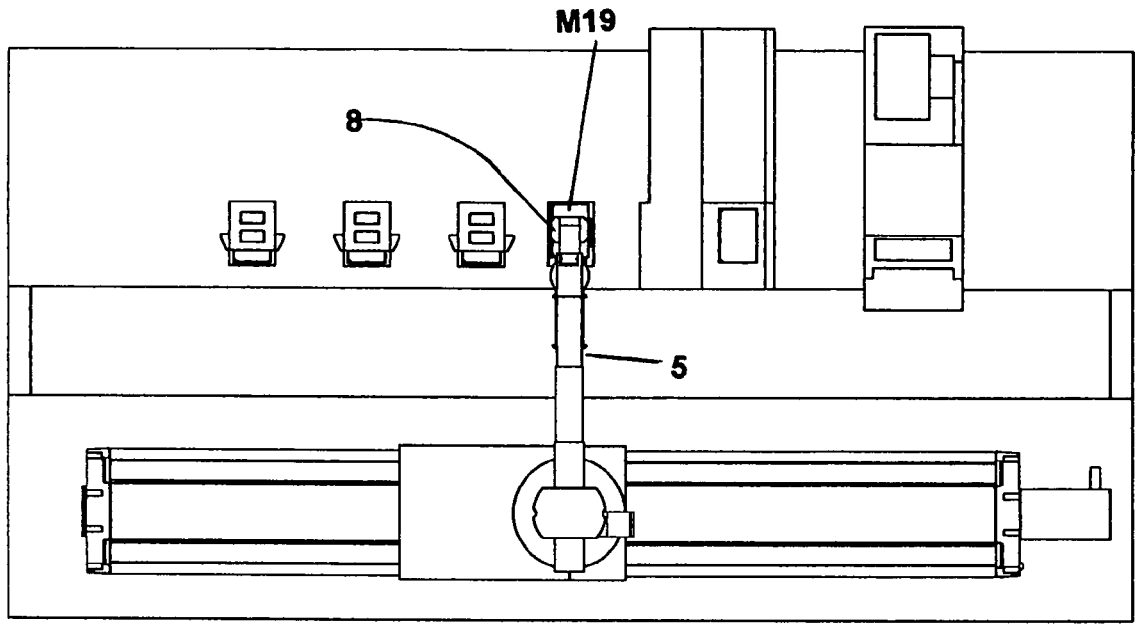

In FIG. 29 motor 52 (FIG. 1E) has rotated rotatable shovel/gripper assembly 34 so that gripper 8 is positioned above micro-well plate M19. Then, motor 50 (FIG. 1L) has caused linear actuator 4 to lower telescopic gripper arm 5 so that gripper 8 has been lowered on top of micro-well plate M19. Motor 53 has activated gripper 8 thereby closing gripper arms 8A and 8B (see also FIG. 1C) tight around micro-well plate M19.

Figure 30:
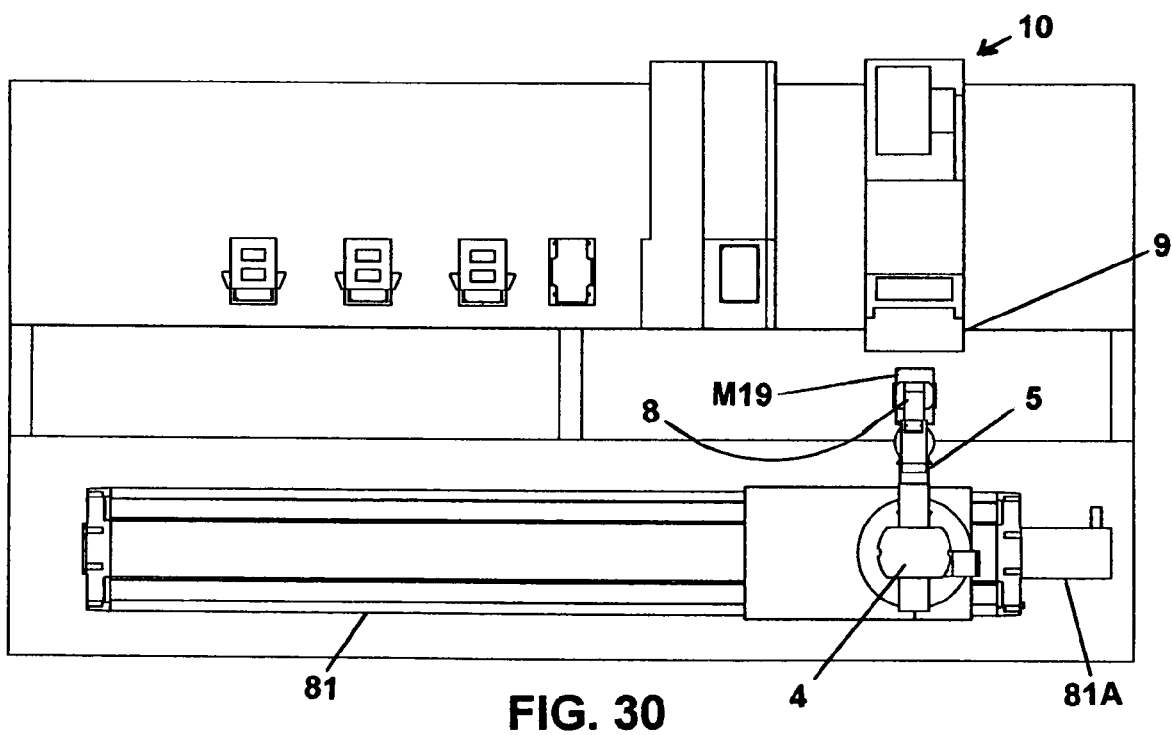

In FIG. 30 motor 81A has controlled gantry 81 so that it has moved linear actuator 4 to the right so that telescopic gripper arm 5 is positioned in front of receiving machine 10. Also, motor 51 (FIG. 1I) has rotated gear 51F causing telescopic gripper arm 5 to retract. Also, motor 50 has caused linear actuator 4 to lower telescopic gripper arm 5 so that gripper 8 holds micro-well plate M19 slightly above the height of platform 9.

Figure 31:
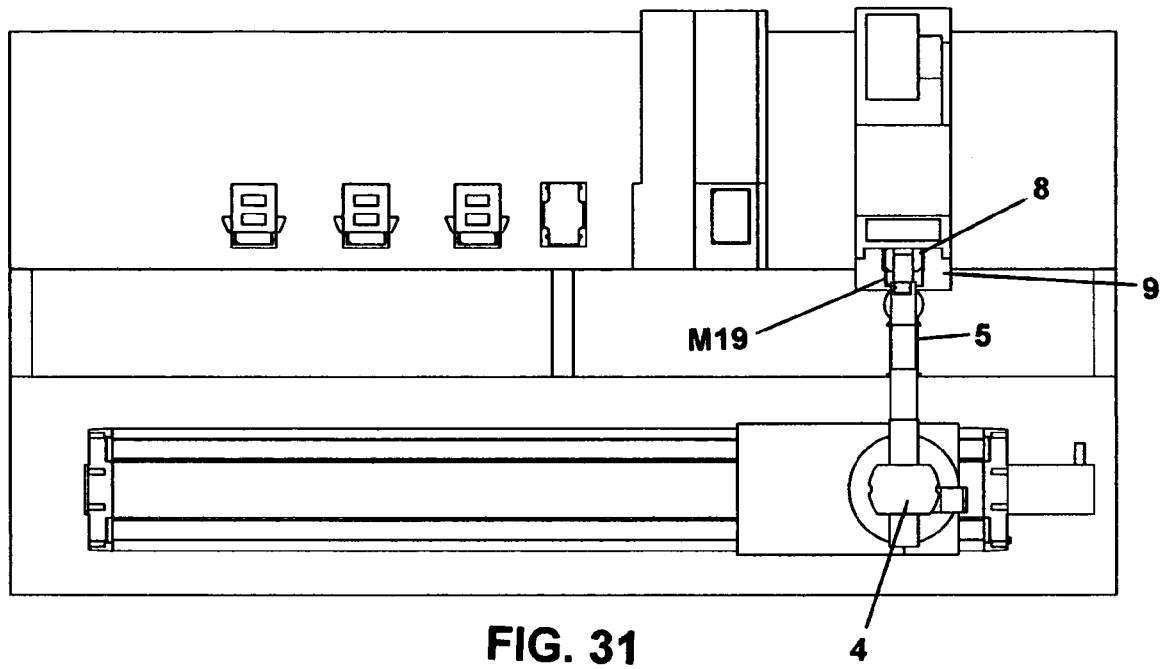

In FIG. 31 motor 51 (FIG. 1I) has rotated gear 51F causing telescopic gripper arm 5 to extend. Also, motor 50 has caused linear actuator 4 to lower telescopic gripper arm 5 so that gripper 8 has placed micro-well plate M19 on the top of platform 9. Motor 53 has activated gripper 8 thereby loosening gripper arms 8A and 8B (see also FIG. 1C) from around micro-well plate M19.

Figure 32:
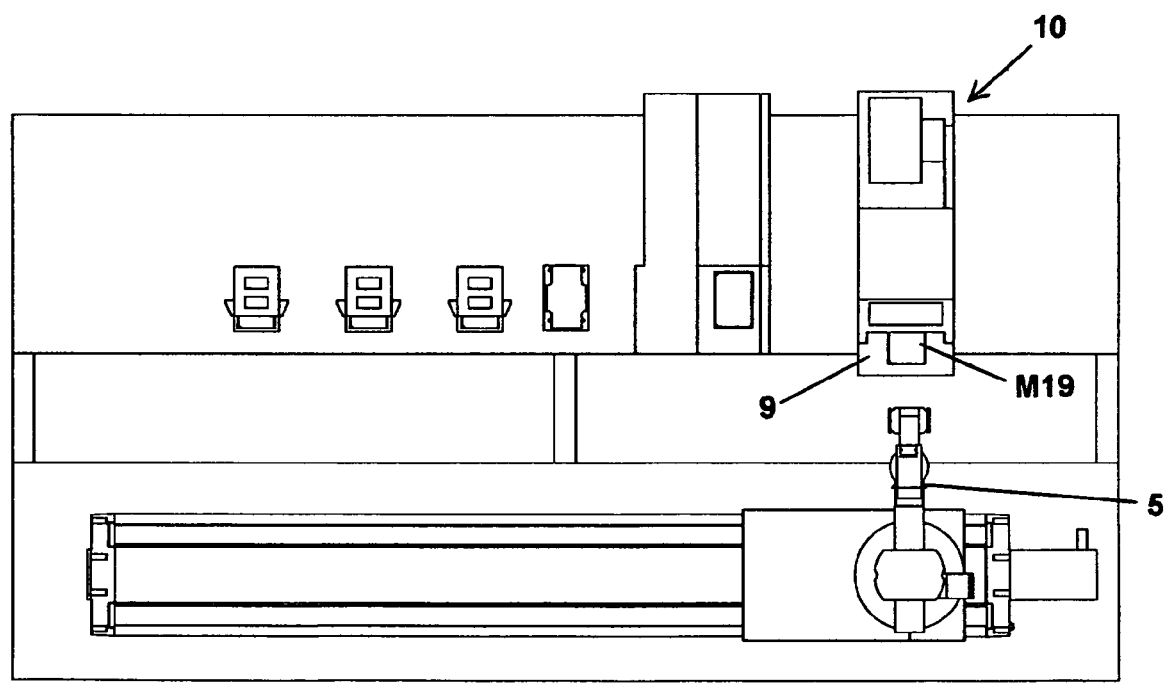

In FIG. 32 motor 51 (FIG. 1I) has rotated gear 51F causing telescopic gripper arm 5 to retract so as to leave micro-well plate M19 on top of platform 9. Micro-well plate M19 has now been left on platform 9, properly orientated so as to be ready for access by receiving machine 10.

After receiving machine 10 is finished with micro-well plate M19, robot 12 will preferably remove micro-well plate M19 from receiving machine 10 and return it to micro-well plate storage unit 2.

Third Preferred Embodiment

Figure 33:
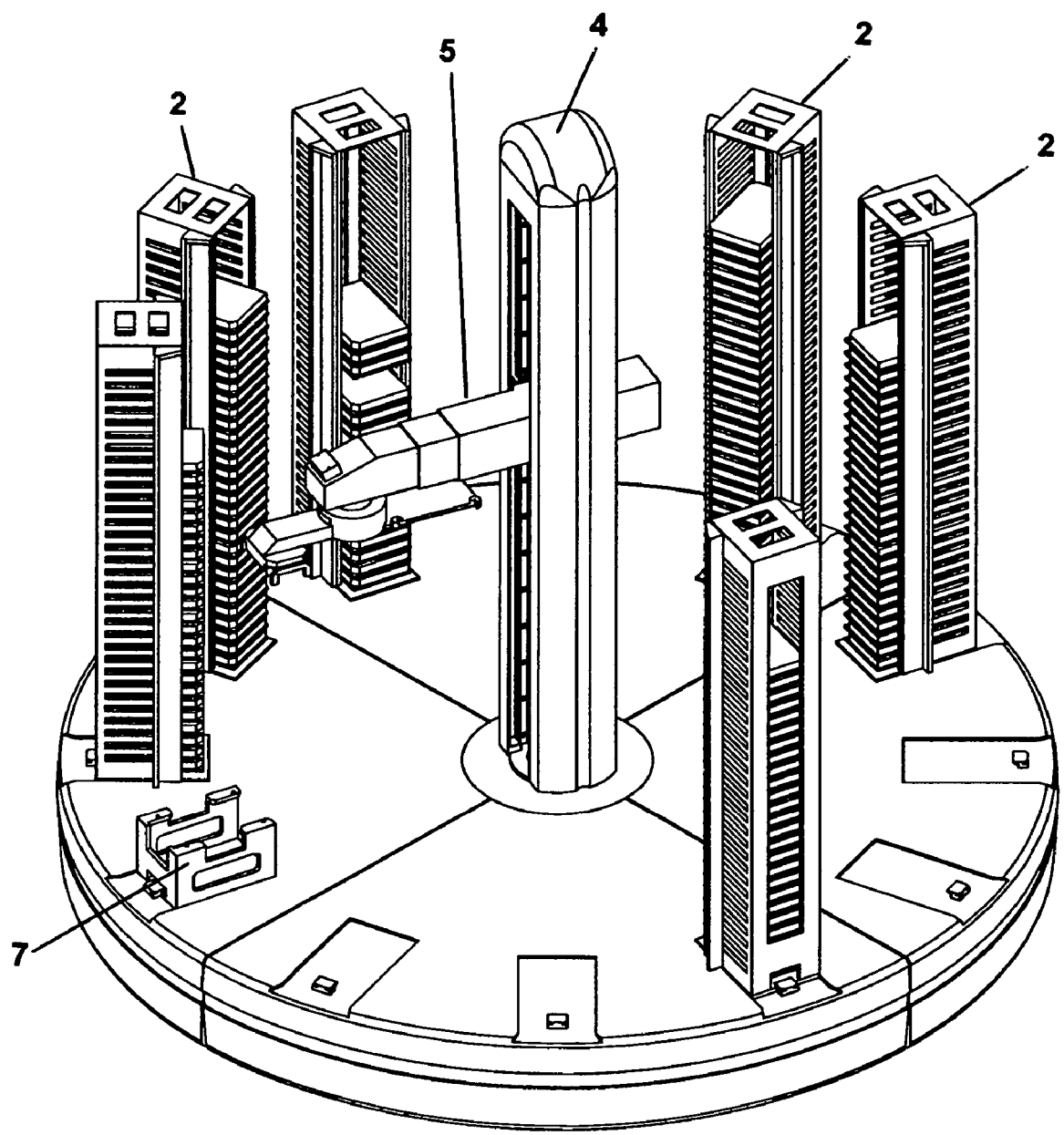
FIG. 33 shows a third preferred embodiment of the present invention.

A third preferred embodiment of the present invention is shown in FIG. 33. The third preferred embodiment is similar to the first preferred embodiment. In the third preferred embodiment, multiple micro-well plate storage units 2 have been placed around linear actuator 4. Utilizing telescopic gripper arm 5 in a fashion similar to that described in the above preferred embodiments, in the third preferred embodiment a user can remove a micro-well plate from any of the micro-well plate storage units 2 and place the micro-well plate on transfer station 7. Because, linear actuator 4 is positioned over slip ring 72 (FIG. 1H) electrical connections can continuously be made while linear actuator 4 rotates 360 degrees or more in a clockwise or counterclockwise fashion.

Fourth Preferred Embodiment

Except for a few variations, the fourth preferred embodiment is very similar to the first preferred embodiment. For robot 112 (FIG. 34), rotatable shovel/gripper assembly 34 (FIG. 1E) and shove/gripper rotation controller 44 have been replaced with rotatable gripper 102 and rotatable gripper controller 113. Also, in the fourth preferred embodiment, shovel 6 has been replaced with shovel 103 and transfer station 7 has been replaced with transfer station 104.

In the fourth preferred embodiment, motor 101 controls the rotation of gripper 102. Motor 101 receives control inputs from gripper rotation controller 113 via slip ring 72. Also, motor 111 controls the loosening and tightening of gripper 102 on micro-well plates. Motor 111 receives control inputs from gripper controller 114 via slip ring 72.

In the fourth preferred embodiment, by having the rotation axis for rotatable gripper 102 directly above rotatable gripper 102, the arc of the gripper rotation is drastically reduced. By eliminating a large gripper rotation arc, micro-well plates can be more easily placed and properly aligned on receiving machines that have small receiving platforms and surrounding obstructions.

Sequence of Operation of Fourth Preferred Embodiment

FIGS. 35-50 describe a sequence of operation of the fourth preferred embodiment.

Figure 35:
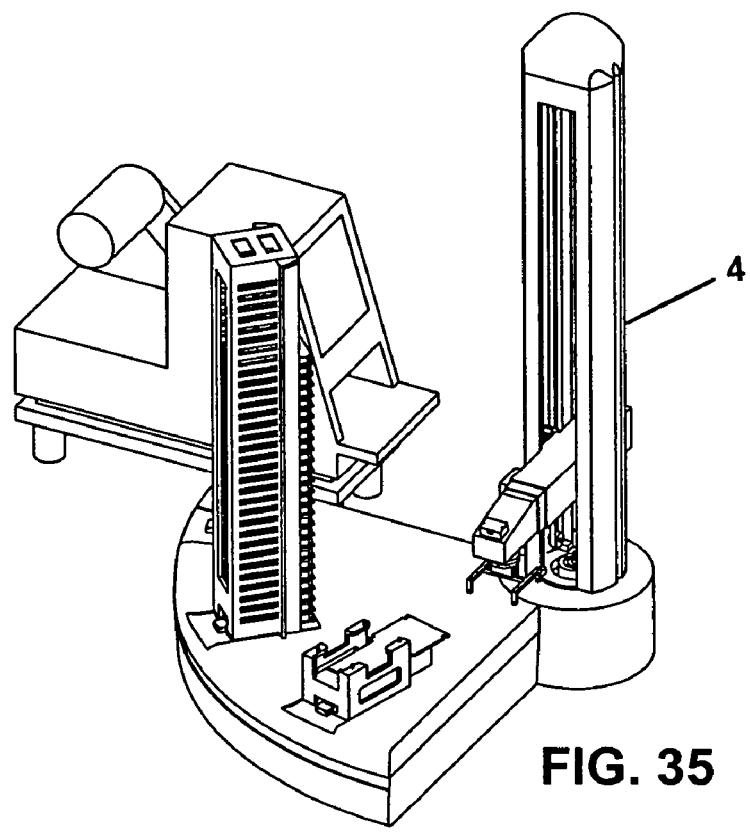
FIGS. 35-51 show a sequence illustrating the operation of the fourth preferred embodiment.

In FIG. 35 linear actuator 4 is at its starting position.

Figure 36:
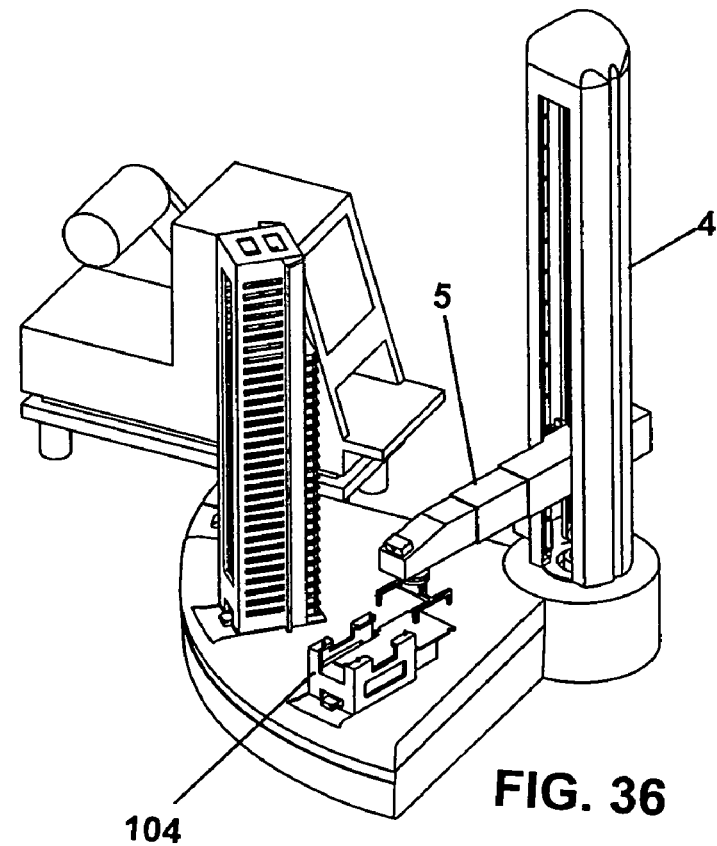

In FIG. 36 motor 51 (FIG. 1I) has rotated gear 51F causing telescopic gripper arm 5 to extend. Motor 43A (FIG. 34) has rotated linear actuator 4 clockwise so that telescopic gripper arm 5 is positioned in front of transfer station 104.

Figure 37:
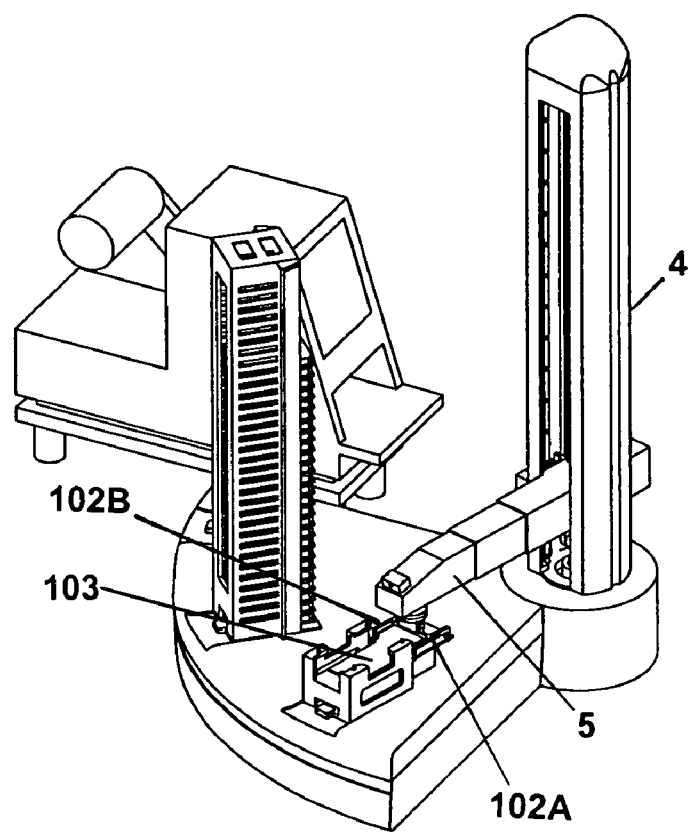

In FIG. 37 motor 50 (FIGS. 34 and 1L) has caused linear actuator 4 to lower telescopic gripper arm 5 so that gripper 102 has been lowered on top of shovel 103. Motor 111 has activated gripper 102 thereby closing gripper arms 102A and 102B tight around shovel 103.

Figure 38:
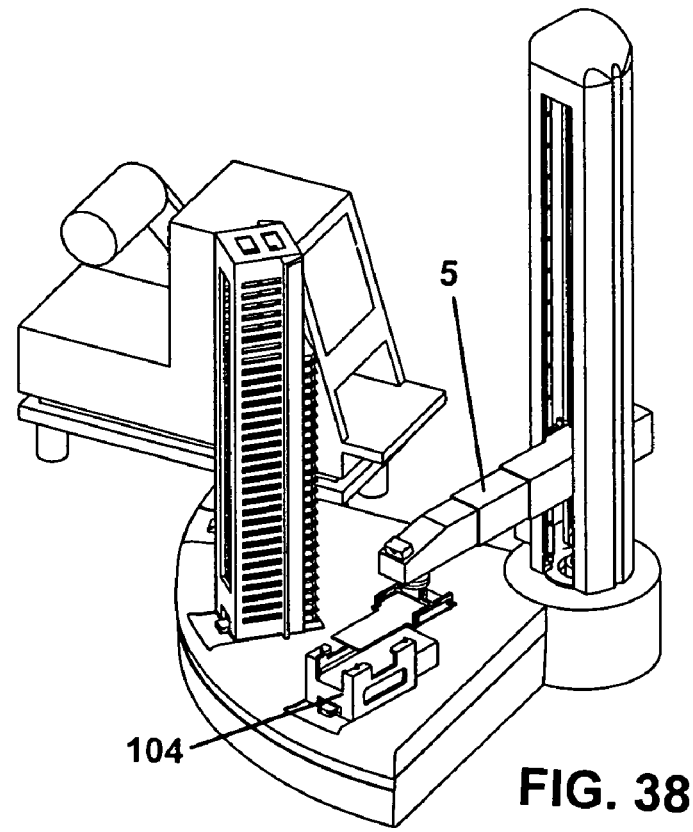

In FIG. 38 motor 50 (FIGS. 34 and 1L) has caused linear actuator 4 to raise telescopic gripper arm 5 so that shovel 103 has been lifted from transfer station 104.

Figure 39:
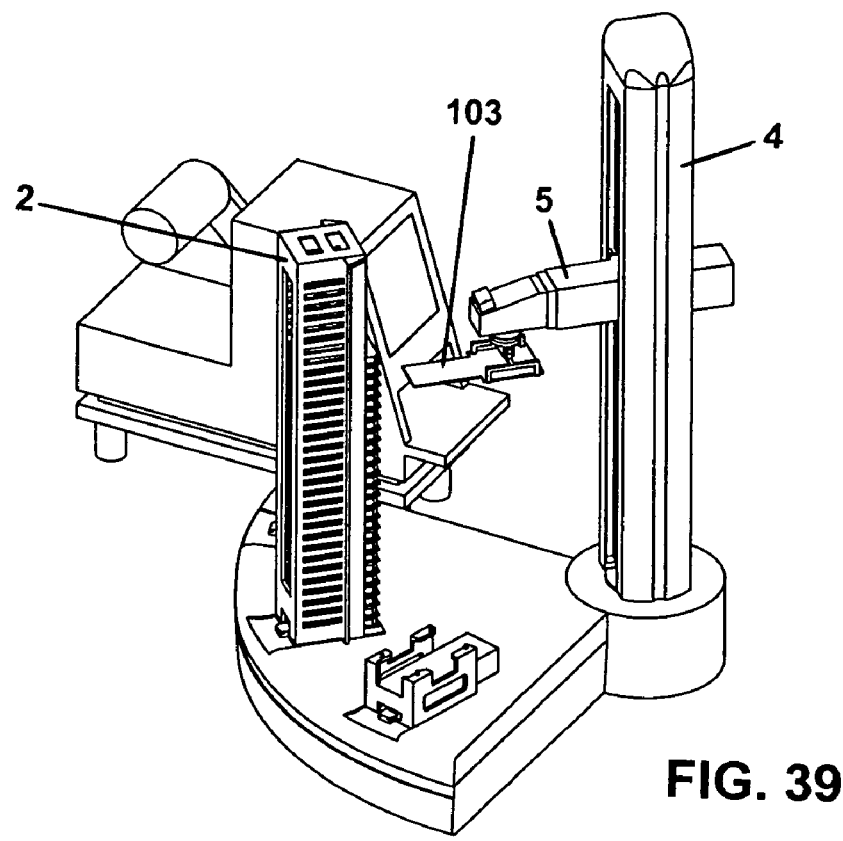

In FIG. 39 motor 43A (FIG. 34) has rotated linear actuator 4 clockwise so that telescopic gripper arm 5 is positioned in front of micro-well plate storage unit 2. Also, motor 50 (FIGS. 34 and 1L) has caused linear actuator 4 to raise telescopic gripper arm 5 so that shovel 103 is at the appropriate height to slide under micro-well plate M22 in micro-well plate storage unit 2.

Figure 40:
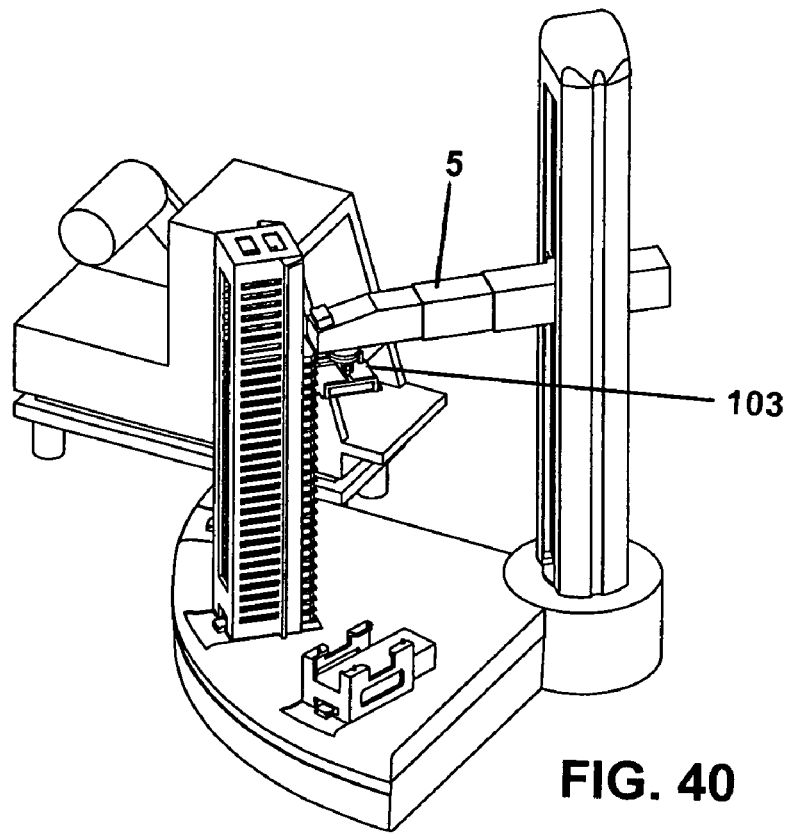

In FIG. 40 motor 51 (FIG. 1I) has rotated gear 51F causing telescopic gripper arm 5 to extend. Shovel 103 has slid under micro-well plate M22 in a fashion similar to that shown regarding shovel 6 in FIG. 7.

Figure 41:
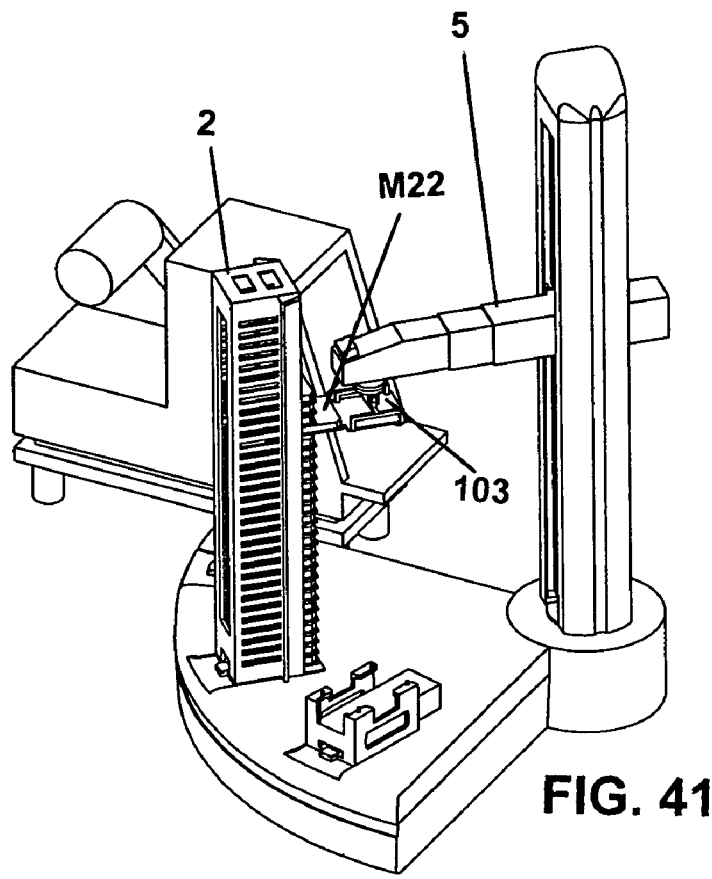

In FIG. 41 motor 50 (FIG. 1L) has caused linear actuator 4 to lift telescopic gripper arm 5 so that shovel 103 has lifted micro-well plate M22 upwards, clearing it from tabs 61 (FIG. 1F). Also, motor 51 (FIG. 1I) has rotated gear 51F causing telescopic gripper arm 5 to retract so that micro-well plate M22 has been partially removed from micro-well plate storage unit 2.

Figure 42:
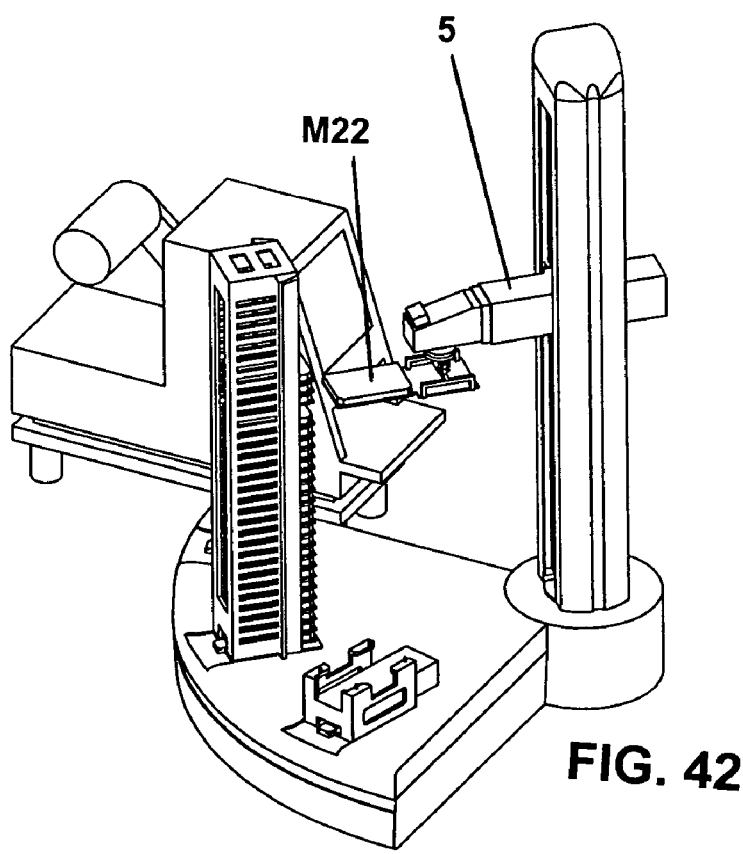

In FIG. 42 motor 51 (FIG. 1I) has rotated gear 51F causing telescopic gripper arm 5 to further retract so that micro-well plate M22 has been fully removed from micro-well plate storage unit 2.

Figure 43:
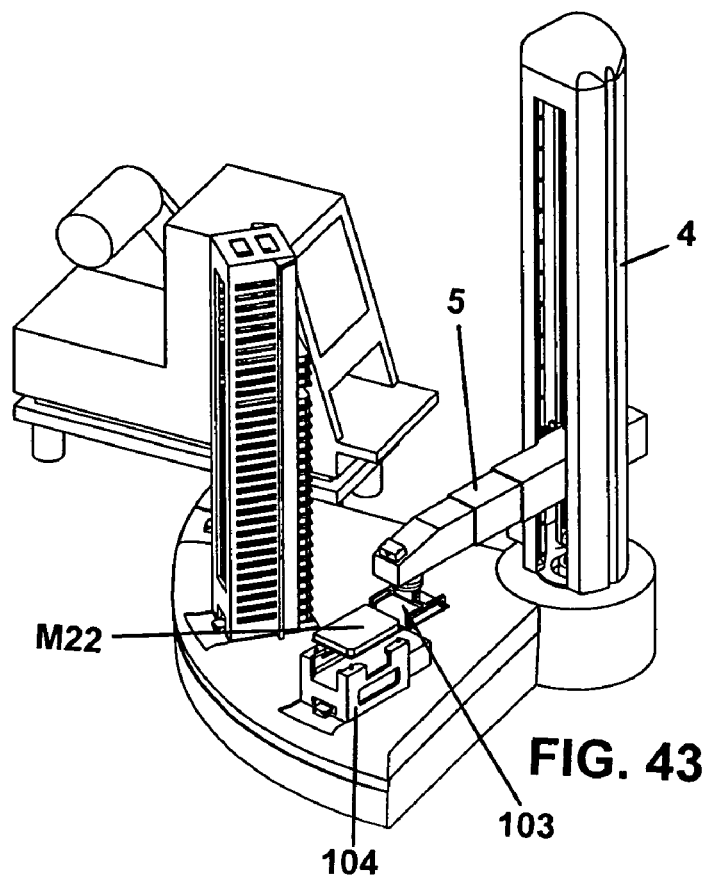

In FIG. 43 motor 43A (FIG. 34) has rotated linear actuator 4 counterclockwise so that telescopic gripper arm 5 is positioned in front of transfer station 104. Also, motor 50 (FIGS. 34 and 1L) has caused linear actuator 4 to lower telescopic gripper arm 5 so that shovel 103 is holding micro-well plate M22 slightly above transfer station 104.

Figure 44:
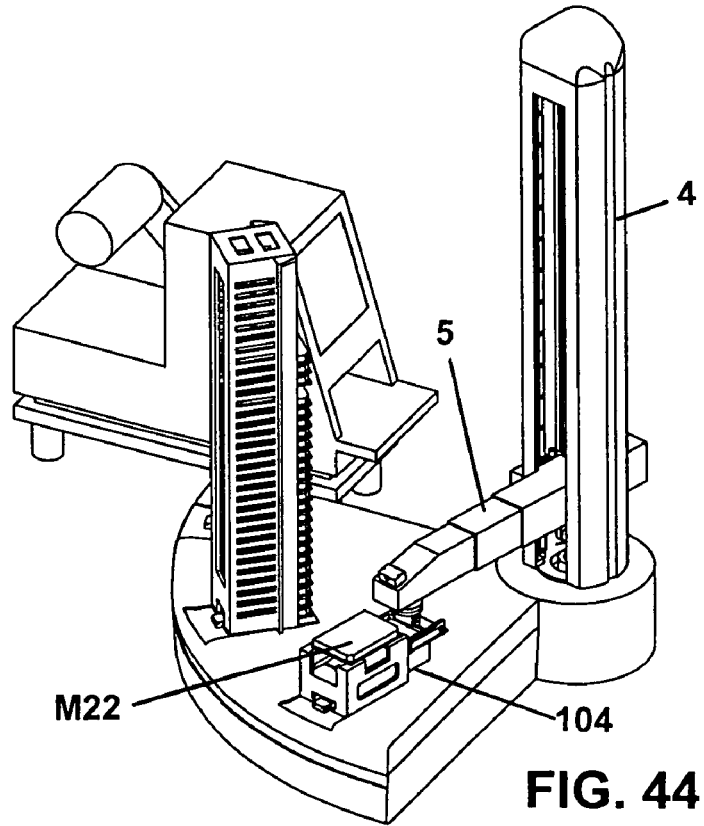

In FIG. 44 motor 50 (FIGS. 34 and 1L) has caused linear actuator 4 to lower telescopic gripper arm 5 so that micro-well plate M22 is resting on top of transfer station 104.

Figure 34:
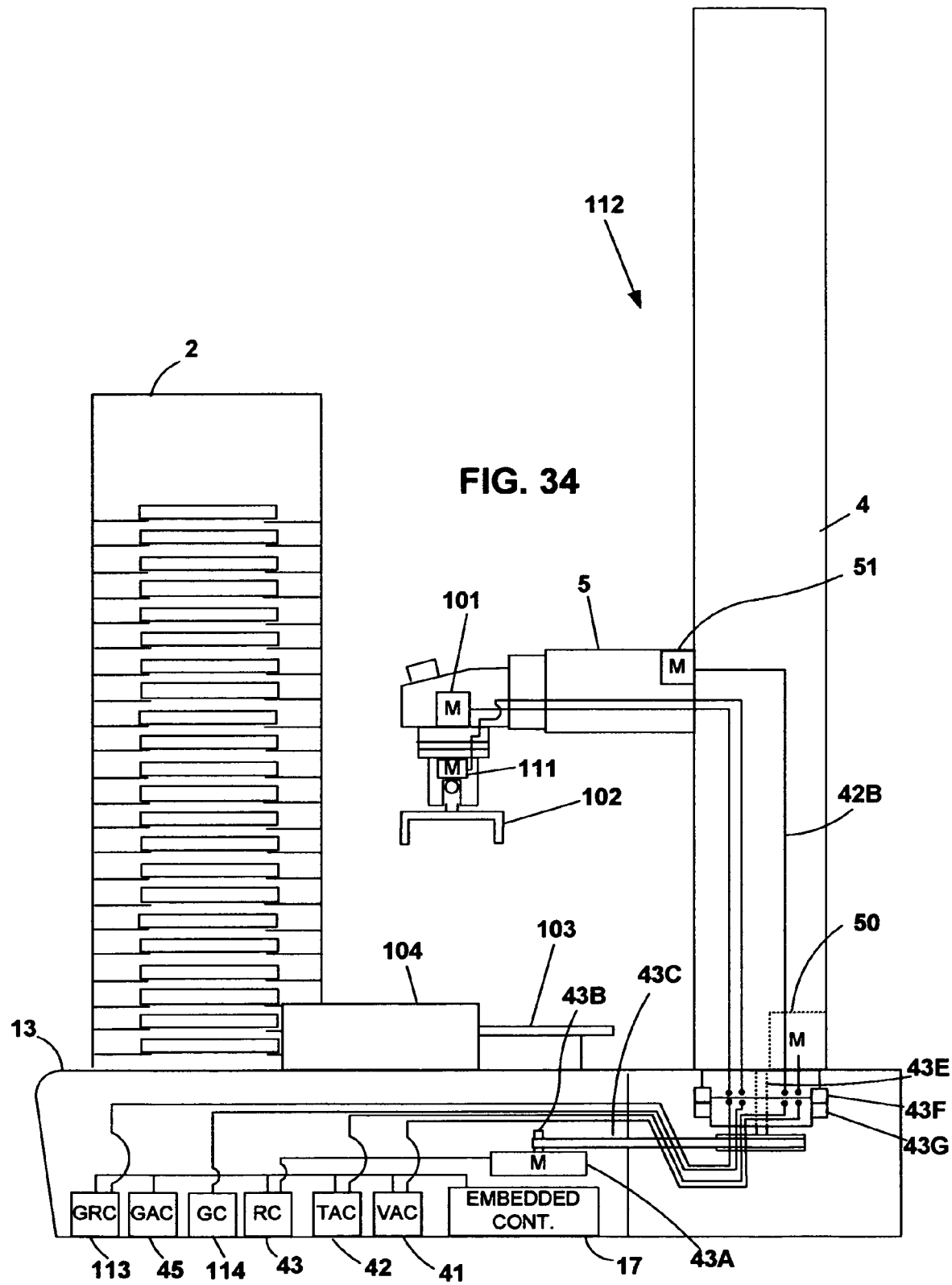
FIG. 34 shows a fourth preferred embodiment of the present invention.
Figure 45:
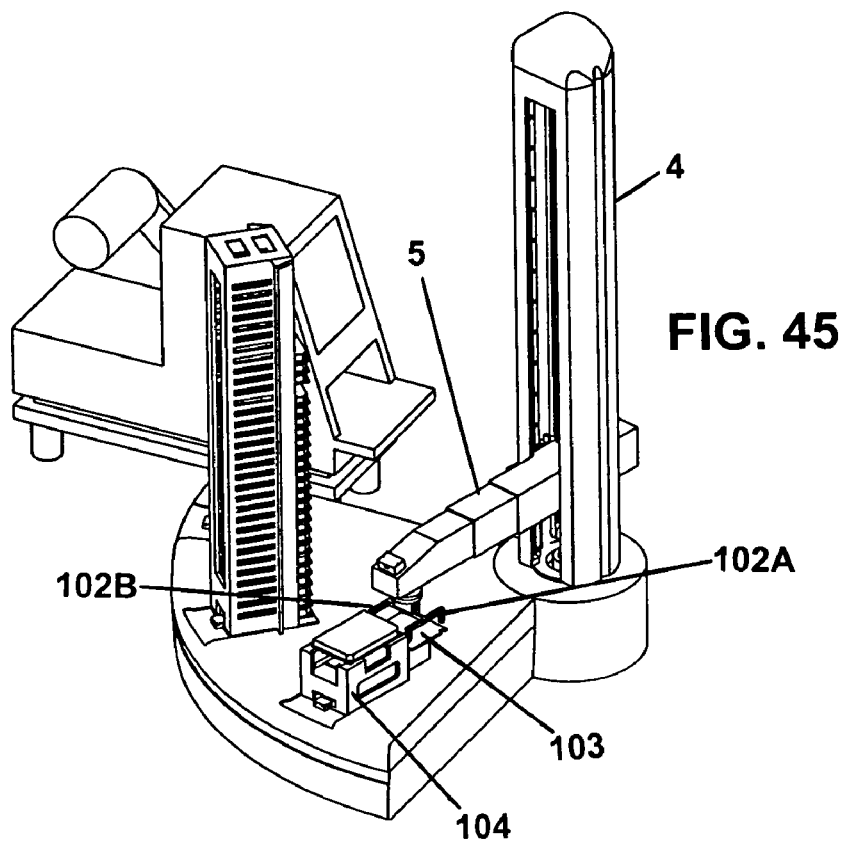

In FIG. 45 motor 111 has activated gripper 102 thereby loosening gripper arms 102A and 102B from around shovel 103. Also, motor 50 (FIGS. 34 and 1L) has caused linear actuator 4 to raise telescopic gripper arm 5 so that shovel 103 is left resting on top of transfer station 104. A simplified side view of shovel 103 resting on top of transfer station 104 is also shown in FIG. 34.

Figure 46:
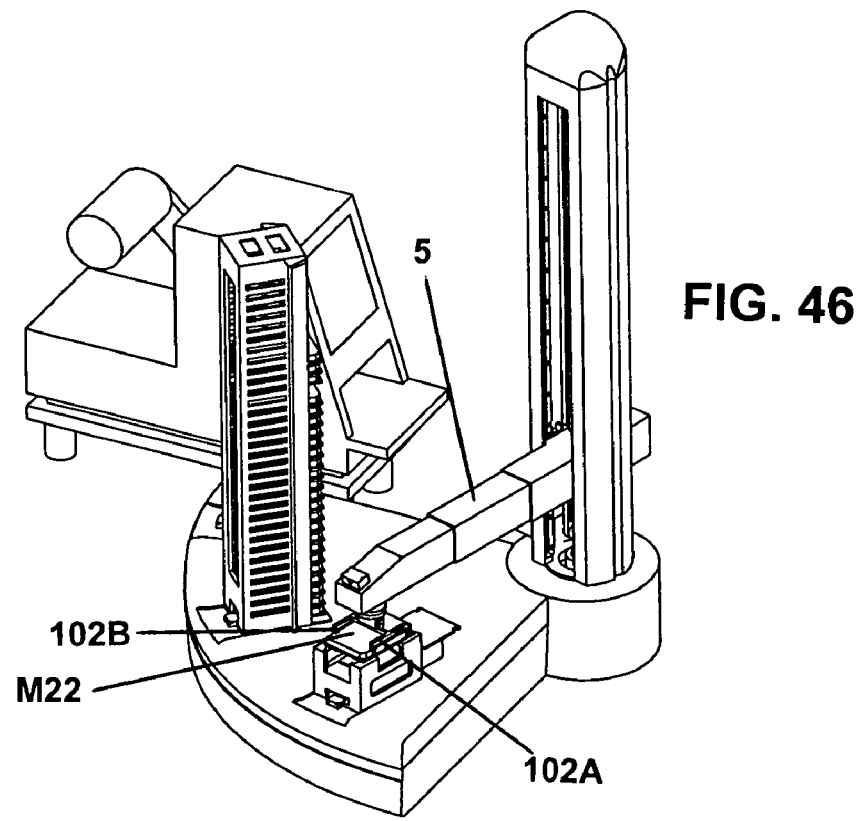

In FIG. 46 motor 50 (FIGS. 34 and 1L) has caused linear actuator 4 to raise telescopic gripper arm 5 so that gripper 102 is at the appropriate height to grab micro-well plate M22. Also, motor 51 (FIG. 1I) has rotated gear 51F causing telescopic gripper arm 5 to extend so that gripper arms 102A and 102B are positioned around micro-well plate M22.

Figure 47:
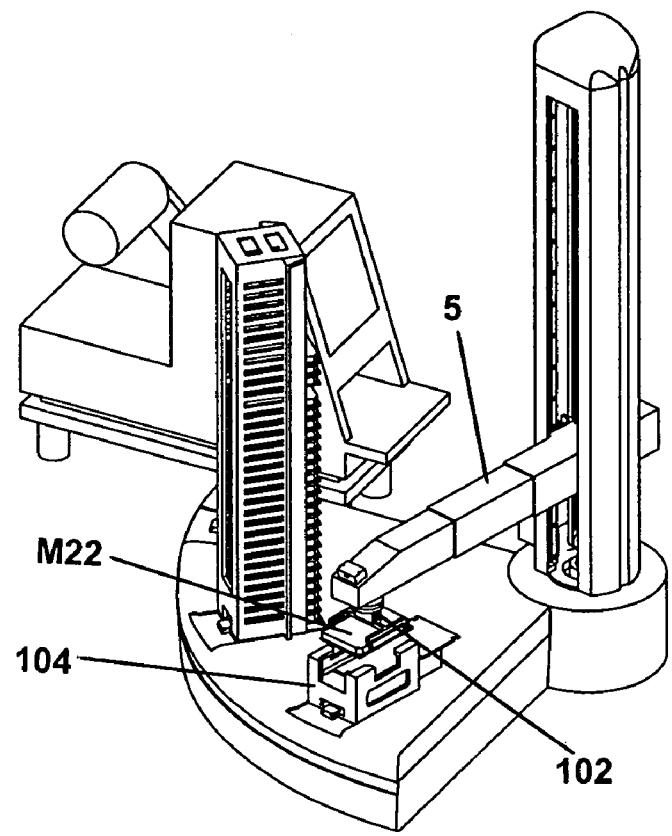

In FIG. 47 motor 50 (FIGS. 34 and 1L) has caused linear actuator 4 to raise telescopic gripper arm 5 so that gripper 102 has lifted micro-well plate M22 from transfer station 104.

Figure 48:
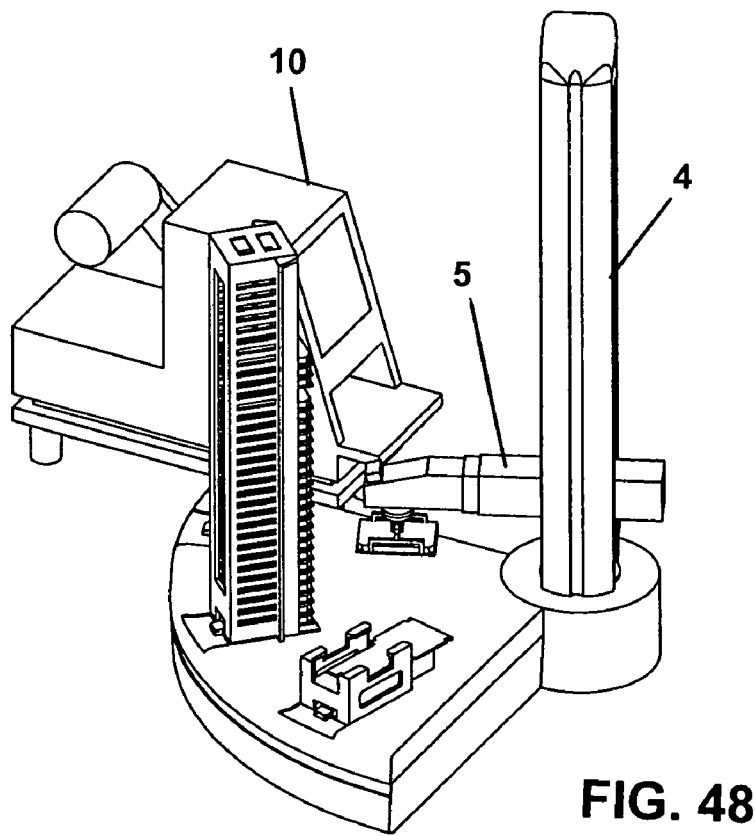

In FIG. 48 motor 43A (FIG. 34) has rotated linear actuator 4 clockwise so that telescopic gripper arm 5 has moved towards receiving machine 10. Also, motor 51 (FIG. 1I) has rotated gear 51F causing telescopic gripper arm 5 to retract.

Figure 49:
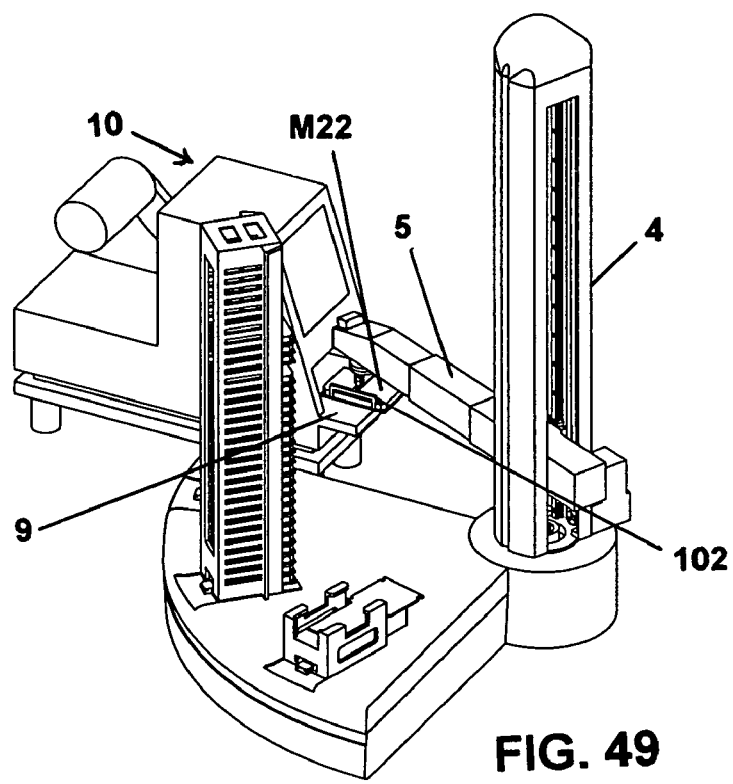
Figure 50:
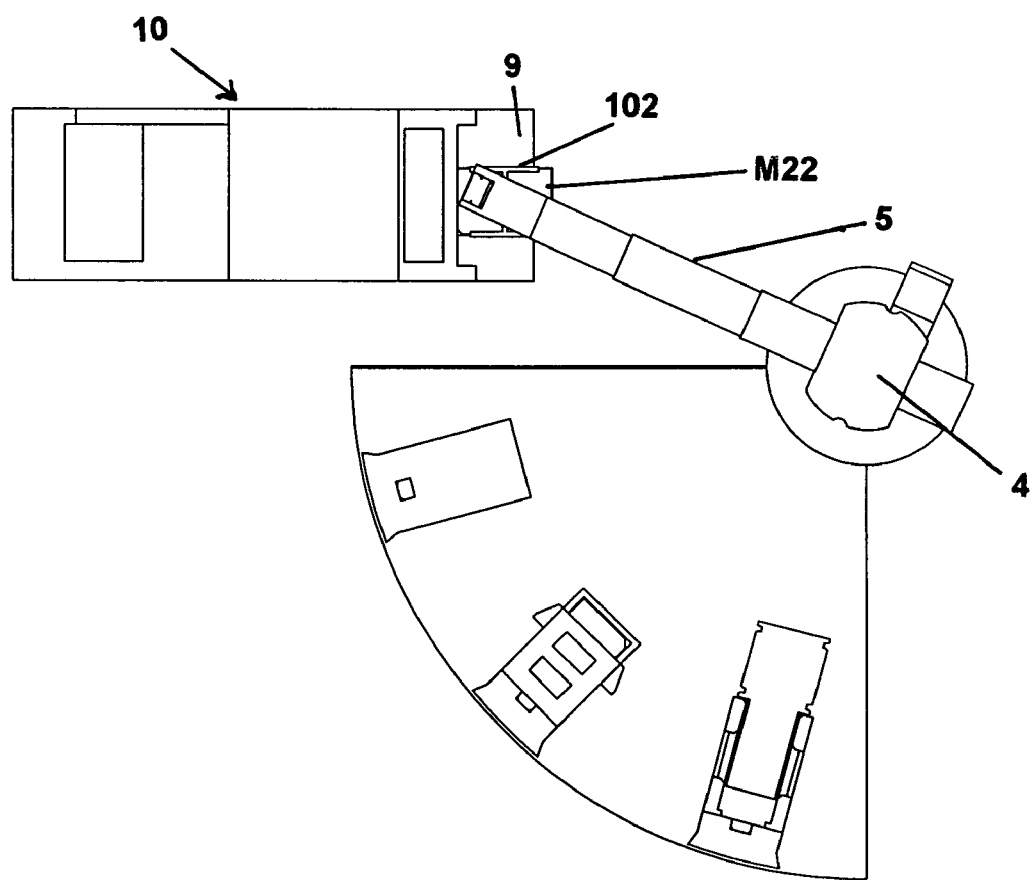

In FIGS. 49 and 50 motor 43A (FIG. 34) has further rotated linear actuator 4 clockwise so that telescopic gripper arm 5 is in front of receiving machine 10. Also, motor 51 (FIG. 1I) has rotated gear 51F causing telescopic gripper arm 5 to extend so that gripper 102 is holding micro-well plate M22 at platform 9. Motor 50 (FIGS. 34 and 1L) has caused linear actuator 4 to adjust the height of telescopic gripper arm 5 so that gripper 102 has placed micro-well plate at the surface level of platform 9. Motor 101 (FIG. 34) has rotated gripper 102 so that micro-well plate M22 is properly aligned on platform 9. Micro-well plate M22 has now been left on platform 9, properly orientated so as to be ready for access by receiving machine 10.

Figure 51:
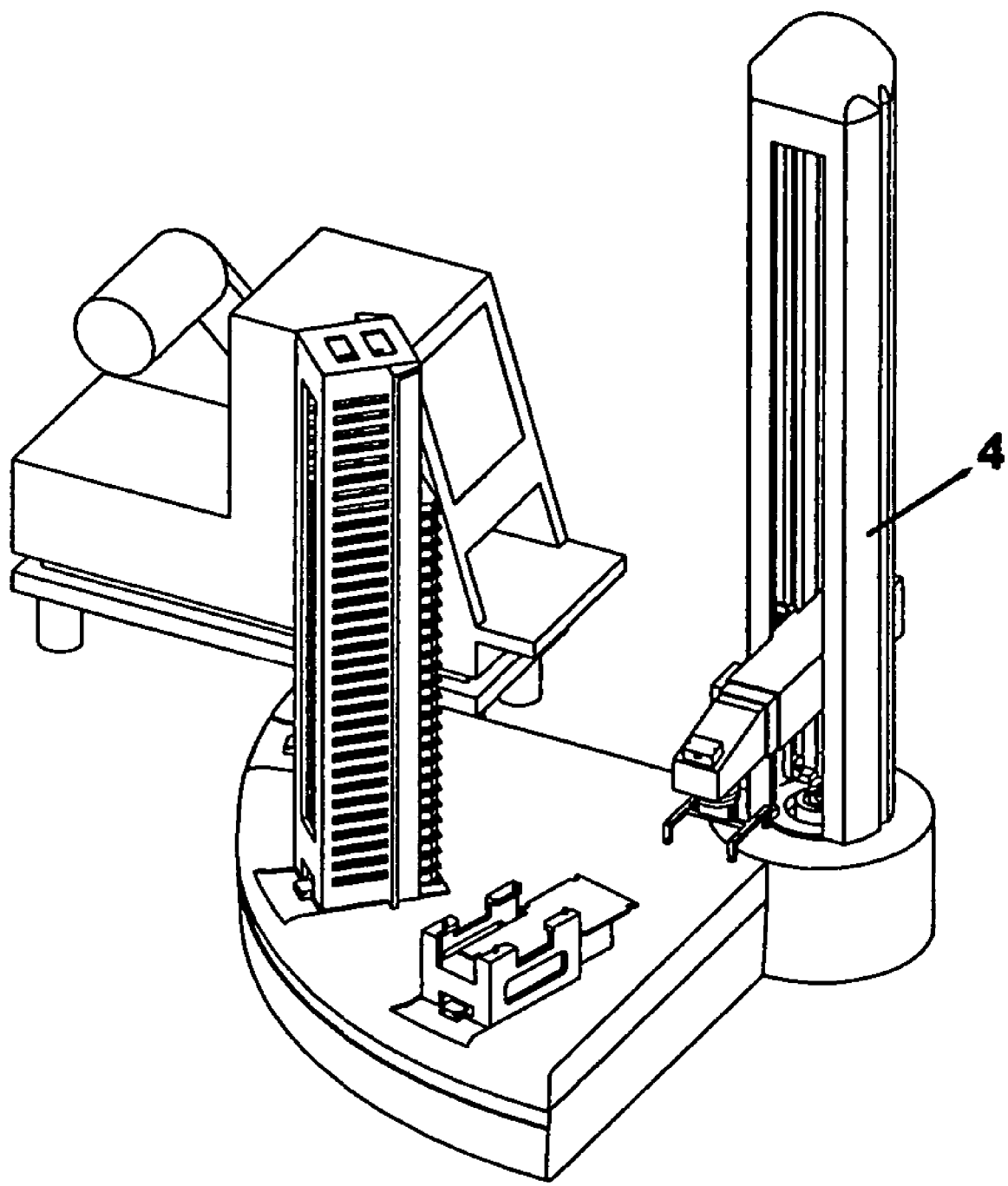

In FIG. 51 motor 43A (FIG. 34) has rotated linear actuator 4 counterclockwise so that telescopic gripper arm 5 has moved back to the starting position shown in FIG. 35. Also, motor 51 (FIG. 1I) has rotated gear 51F causing telescopic gripper arm 5 to retract. Motor 50 (FIGS. 34 and 1L) has caused linear actuator 4 to adjust the height of telescopic gripper arm 5. Motor 101 (FIG. 34) has rotated gripper 102 so that gripper 102 is in alignment with telescopic gripper arm 5.

Barcode Reader

Preferably robot 12 also includes barcode reader 131 (FIG. 1B). Barcode reader 131 automatically reads barcode data on micro-well plates stacked in micro-well plate storage unit 2. This data is then transmitted to embedded controller 17 via slip ring 72. An individual accessing the web site loaded onto embedded controller 17 will then be able ascertain and verify via the barcode data the specific micro-well plates stacked in micro-well plate storage unit 2.

Although the above-preferred embodiments have been described with specificity, persons skilled in this art will recognize that many changes to the specific embodiments disclosed above could be made without departing from the spirit of the invention. For example, although the above preferred embodiments showed a micro-well plate being transferred to receiving machine 10, a micro-well plate can be transferred to other types of receiving areas. For example, it can be transferred to a variety of receiving machine types or it can be transferred to a table for inspection by a technician. Also, although the above preferred embodiments disclosed that the present invention is controllable via the Internet, Intranet and Ethernet, it should easily be recognized that the present invention can be controlled via a variety of computer network types. For example, it can be controlled via a variety of Local Area Networks and as well as Wide Area Networks. Also, although it was disclosed how micro-well plate storage unit 2 was utilized to vertically store micro-well plates and vertical clearance spaces between the micro-well plates, it should be recognized that devices other than a micro-well plate storage unit can also be utilized to vertically store the micro-well plates and provide vertical clearance spaces between the micro-well plates. For example, a rack with tabs similar to tabs 61 could be used or shelves with tabs similar to tabs 61 could be used. Also, although the above embodiments state that the present invention is for handling micro-well plates, it should be recognized that it can be utilized to handle other types of media storage devices. For example, shovel 6 could be configured to fit under a slide and gripper 8 can be configured to grab a slide. This embodiment could then be utilized for transferring a slide from within a vertical stack of slides to a receiving area. Also, although the above preferred embodiments specifically discussed the utilization of embedded controller 17, it should be recognized that a variety of computer control devices can also be utilized in place of embedded controller 17. For example, a programmable personal computer can also be utilized. Preferably the personal computer will be programmed to include its own website that will be accessible by other computers (for example, remote computer 23, control computer 16 or laptop portable computer 20). The website will allow users to interface with and control robot 12 in a manner similar to embedded controller 17. Also, although the above preferred embodiments showed the utilization of micro-well plate storage unit 2, it should be understood that a variety of micro-well plate storage units could be utilized. The spacing between tabs 61 may vary depending on the micro-well plate type being utilized and whether or not the micro-well plates have lids. Also, although the above-preferred embodiments describe how the micro-well plate is transferred to a transfer station between exchanging control of the plate from the shovel to the gripper, it would be possible to design a robot so that a gripper grabbed the micro-well plate off the top of the shovel without first transferring the micro-well plate to a transfer station. Therefore, the attached claims and their legal equivalents should determine the scope of the invention.

What is claimed is:

1. An automated micro-well plate handling device for removing a removable micro-well plate from within a vertically stacked plurality of removable micro-well plates and transferring said removable micro-well plate to a receiving area, comprising:
   A) a stationary transfer station,
   B) a vertical storage device for storing in a vertical stack a plurality of removable micro-well plates, wherein said vertical storage device creates a vertical clearance space under each of said removable micro-well plates,
   C) a rotatable micro-well plate handling device, comprising:
      1) a shovel unit at a first end, said shovel unit for sliding into said vertical clearance space underneath said removable micro-well plate and for removing said removable micro-well plate from said vertical storage device and placing said removable micro-well plate at said stationary transfer station, and
      2) a gripper unit at a second end, said gripper unit for gripping said removable micro-well plate at said stationary transfer station and transporting it to said receiving area, and
   D) an extendable and retractable telescopic gripper arm, wherein said rotatably attached micro-well plate handling device is rotabably mounted onto said telescopic gripper arm,
   wherein said shovel unit does not make contact with said stationary transfer station when depositing said micro-well plate onto said stationary transfer station or when retrieving said micro-well plate from said stationary transfer station.

2. The automated micro-well plate handling device as in claim 1 wherein said telescopic gripper arm comprises a retractable and extendable tape.

3. The automated micro-well plate handling device as in claim 1 further comprising a linear actuator for vertically positioning said shovel and said gripper.

4. The automated micro-well plate handling device as in claim 3 wherein said linear actuator rotates about the vertical central axis of said linear actuator to position said gripper and said shovel adjacent to said vertical storage device, said shovel unit to gripper unit transfer station and said receiving area.

5. The automated micro-well plate handling device as in claim 4 wherein said rotatable linear actuator is positioned over a slip ring, wherein electrical signals are transferred through said slip ring.

6. The automated micro-well plate handling device as in claim 1 further comprising an embedded controller for controlling said automated micro-well plate handling device.

7. The automated micro-well plate handling device as in claim 6, wherein said embedded controller comprises a web site for controlling said automated micro-well plate handling device, wherein said web site is accessible via a remote computer.

8. The automated micro-well plate handling device as in claim 7, wherein said remote computer accesses said web site via a computer network.

9. The automated micro-well plate handling device as in claim 1 wherein said gripper is a rotatable gripper.

10. The automated micro-well plate handling device as in claim 9 wherein said rotatable gripper rotates to allow said shovel to slide into said vertical clearance space.

11. The automated micro-well plate handling device as in claim 1 further comprising a gantry for horizontal positioning of said shovel and said gripper.

12. An automated micro-well plate handling device for removing a removable micro-well plate from within a vertically stacked plurality of micro-well plates and transferring said removable micro-well plate to a receiving area, comprising:
A) a vertical storage device for storing said vertically stacked plurality of micro-well plates, wherein said vertical storage device comprises a means for creating a vertical clearance space under said removable micro-well plate,
B) a stationary transfer station,
E) a rotatably attached micro-well plate handling device, comprising:
  3) a shovel unit at a first end, said shovel unit for sliding into said vertical clearance space underneath said removable micro-well plate and for removing said removable micro-well plate from said vertical storage device and placing said removable micro-well plate at said stationary transfer station, and
  4) a gripper unit at a second end, said gripper unit for gripping said removable micro-well plate at said stationary transfer station and transporting it to said receiving area
E) a receiving area for receiving said removable micro-well plate from said gripper unit,
G) an extendable and retractable telescopic gripper arm for horizontally positioning said rotatably attached micro-well plate handling device, wherein said a rotatably attached micro-well plate handling device is rotatably mounted onto said extendable and retractable telescopic gripper arm,
H) a linear actuator for vertically positioning said rotatably attached micro-well plate handling device, and
I) a slip ring positioned underneath said linear actuator, wherein electrical signals are transferred through said slip ring
wherein said shovel unit does not make contact with said stationary transfer station when depositing said micro-well plate onto said stationary transfer station or when retrieving said micro-well plate from said stationary transfer station.

13. A method for removing a removable micro-well plate from within a vertically stacked plurality of micro-well plates and transferring said removable micro-well plate to a receiving area, comprising the steps of:
A) storing in a vertical storage device said vertically stacked plurality of micro-well plates so that a vertical clearance space is created under said removable micro-well plate,
B) positioning a rotatably attached micro-well plate handling device, said rotatably attached micro-well plate handling device comprising:
  1) a shovel unit at a first end, said shovel unit for sliding into said vertical clearance space underneath said removable micro-well plate and for removing said removable micro-well plate from said vertical storage device and placing said removable micro-well plate at said stationary transfer station, and
  2) a gripper unit at a second end, said gripper unit for gripping said removable micro-well plate at said stationary transfer station and transporting it to said receiving area C) sliding said shovel unit into said vertical clearance space underneath said removable micro-well plate,
D) using said shovel to remove said removable micro-well plate from said vertical storage device,
E) transferring said removable micro-well plate from said vertical storage device to a stationary transfer station,
F) lowering said micro-well plate onto said stationary transfer station,
G) rotating said rotatably attached micro-well plate handling device so that said gripper unit is adjacent to said micro-well plate,
H) using said gripper unit to grab said removable micro-well plate from said stationary transfer station after said removable micro-well plate has been removed from said vertical storage device, and
I) receiving at a receiving area said removable micro-well plate from said gripper,
wherein said shovel unit does not make contact with said shovel unit to gripper unit transfer station when transferring said micro-well plate onto said shovel unit to gripper unit transfer station or when lifting said micro-well plate from said shovel unit to gripper unit transfer station.

14. An automated micro-well plate handling device for removing a removable micro-well plate from within a vertically stacked plurality of micro-well plates and transferring said removable micro-well plate to a receiving area, comprising:
A) a vertical storage means for storing said vertically stacked plurality of micro-well plates, wherein said means for storing creates a vertical clearance space under said removable micro-well plate,
B) a stationary transfer station means,
C) a means for sliding into said vertical clearance space underneath said removable micro-well plate and for removing said removable micro-well plate from said means for storing,
D) a rotatably attached micro-well plate handling means, comprising:
  5) a shovel unit means at a first end, said shovel unit means for sliding into said vertical clearance space underneath said removable micro-well plate and for removing said removable micro-well plate from said vertical storage means and placing said removable micro-well plate at said stationary transfer station means, and
  6) a gripper unit means at a second end, said gripper unit means for gripping said removable micro-well plate at said stationary transfer station means and transporting it to said receiving area, and F) a means for receiving said removable micro-well plate from said means for gripping, wherein said shovel unit means does not make contact with said stationary transfer station means when transferring said micro-well plate onto stationary transfer station means or when lifting said micro-well plate from said stationary transfer station means.

15. An automated media storage device handler for removing a removable media storage device from within a vertically stacked plurality of media storage devices and transferring said removable media storage device to a receiving area, comprising:
  A) a vertical storage device for storing said vertically stacked plurality of media storage devices, wherein said vertical storage device creates a vertical clearance space under said removable media storage device,
  B) a stationary transfer station,
  C) a rotatably attached micro-well plate handling device, comprising:
    1) a shovel unit at a first end, said shovel unit for sliding into said vertical clearance space underneath said removable micro-well plate and for removing said removable micro-well plate from said vertical storage device and placing said removable micro-well plate at said stationary transfer station, and
    2) a gripper unit at a second end, said gripper unit for gripping said removable micro-well plate at said stationary transfer station and transporting it to said receiving area, and
  F) a receiving area for receiving said removable media storage device from said gripper, wherein said shovel unit does not make contact with said stationary transfer station when depositing said micro-well plate onto said stationary transfer station or when retrieving said micro-well plate from said stationary transfer station.

16. The automated media storage device handler as in claim 15, wherein said media storage device is a slide.

17. The automated micro-well plate handling device as in claim 1 wherein said stationary transfer station comprises:
  A) a micro-well plate upper placement section for allowing either said shovel unit or said gripper unit to deposit said micro-well plate onto said micro-well plate upper placement section and for allowing either said shovel unit or said gripper unit to retrieve said micro-well plate from said micro-well plate upper placement section, and
  B) a shovel unit access section for allowing said shovel unit to have access to the bottom of said micro-well plate so that said shovel unit is able to move away from said micro-well plate after depositing said micro-well plate onto said micro-well plate upper placement section and for allowing said shovel unit access to move under said micro-well plate prior to lifting up on said micro-well plate when retrieving said micro-well plate from said micro-well plate upper placement section.

* * * * *